United States Patent
Kelly

(10) Patent No.: US 11,229,652 B2
(45) Date of Patent: *Jan. 25, 2022

(54) TREATMENTS FOR AUTOIMMUNE DISEASE

(71) Applicant: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

(72) Inventor: Vincent Kelly, Drogheda (IE)

(73) Assignee: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,012

(22) Filed: May 10, 2018

(65) Prior Publication Data

US 2018/0256583 A1 Sep. 13, 2018

Related U.S. Application Data

(63) Continuation of application No. 15/514,968, filed as application No. PCT/EP2015/072488 on Sep. 29, 2015, now abandoned.

(30) Foreign Application Priority Data

Sep. 29, 2014 (GB) .................................. 1417165

(51) Int. Cl.
*A61K 31/519* (2006.01)
*A61K 45/06* (2006.01)

(52) U.S. Cl.
CPC ............ *A61K 31/519* (2013.01); *A61K 45/06* (2013.01)

(58) Field of Classification Search
CPC .......................... C07D 487/04; A61K 31/519
See application file for complete search history.

(56) References Cited

U.S. PATENT DOCUMENTS

| | | | |
|---|---|---|---|
| 4,435,569 A | 3/1984 | Nishimura et al. | |
| 4,571,423 A | 2/1986 | Nomura et al. | |
| 5,002,950 A | 3/1991 | Malone et al. | |
| 5,061,707 A | 10/1991 | Kostlan et al. | |
| 5,312,900 A | 5/1994 | Armstrong | |
| 6,106,864 A | 8/2000 | Dolan et al. | |
| 6,596,701 B1 | 7/2003 | Schwartz et al. | |
| 8,158,636 B2 | 4/2012 | Ibrahim et al. | |
| 2003/0078231 A1 | 4/2003 | Wilburn | |
| 2009/0286782 A1 | 11/2009 | Ibrahim et al. | |
| 2011/0256130 A1* | 10/2011 | Schultz ................ | A61K 31/175 424/133.1 |
| 2017/0258797 A1 | 9/2017 | Kelly | |

FOREIGN PATENT DOCUMENTS

| | | |
|---|---|---|
| EP | 0079447 A1 | 5/1983 |
| EP | 0089955 A2 | 9/1983 |
| EP | 0119591 A1 | 9/1984 |
| EP | 0260491 A1 | 3/1988 |
| JP | S5936615 A | 2/1984 |
| JP | S6056980 A | 4/1985 |
| WO | 8803142 | 5/1988 |
| WO | 9111172 A1 | 8/1991 |
| WO | 9402518 A1 | 2/1994 |
| WO | 9855148 A1 | 12/1998 |
| WO | 0035298 A1 | 6/2000 |
| WO | 2008082247 A1 | 7/2009 |
| WO | 20120150866 A1 | 11/2012 |

OTHER PUBLICATIONS

Muralidhar et al. (Analytical Biochemistry, 1988, 171(2), pp. 346-351).*
Combined Search and Examination Report for GB 1417163.1, dated Jul. 20, 2015 (2 pages).
Combined Search and Examination Report for GB 1417165.6, dated Aug. 11, 2015 (10 pages).
International Search Repart for PCT/EP2015/072486, dated Nov. 11, 2015 (3 pages).
International Search Report for PCT/EP2015/072488, dated Jan. 27, 2016 (4 pages.).
International Preliminary Report on Patentability for PCT/EP/2015/072486, dated Apr. 4, 2017 (8 pages).
International Preliminary Report on Patentability for PCT /EP/2015/072488, dated Apr. 4, 2017 (8 pages).
Non-Final Office Action dated Mar. 14, 2018 for U.S. Appl. No. 15/514,739 (31 pages.).
Hiroshi Akimoto et al., "Queuine Analogues. Their Synthesis and Inhibition of Growth of Mouse L5178Y Cells in Vitro", Journal of Medicinal Chemistry, vol. 29, No. 9, (1986), pp. 1749-1753.
Hiroshi Akimoto et al., "Synthesis of Queuine, The Base of Naturally Occurring Hypermodifed Nucleoside (Queuosine), and Its Analogues", Journal of the Chemical Society, Parkin Transactions 1, Issue 7, (1988), pp. 1637-1644.
Collin Boland et al., "Queuosine formation in eukaryotic tRNA occurs via mitochondrial localized heteromeric transglycosylase", Journal of Biological Chemistry, vol. 284, No. 27, (2009), pp. 18213-18227.

(Continued)

*Primary Examiner* — Susanna Moore
(74) *Attorney, Agent, or Firm* — Hoffman Warnick LLC

(57) ABSTRACT

The invention provides a novel approach to the treatment of autoimmune diseases, particularly multiple sclerosis, using a molecule capable of acting as substrate for the queuine-insertase enzyme complex.

20 Claims, 8 Drawing Sheets

(56) References Cited

OTHER PUBLICATIONS

Allen F Brooks et al., "A short, concise synthesis of queuine", Tetrahedron Letters, vol. 51, No. 32, (2010), pp. 4163-4165.

Allen F. Brooks et al., "Synthesis of Tritium Labeled Queuine, PreQ1 and Related Azide Probes Toward Examining the Prevalence of Queuine", Dissertation at the University of Michigan (2012), pp. 1-88.

Hans-Dieter Gerbert et al., "Concise and efficient syntheses of preQ1 base, Q base, and (ent)-base", Organic & Biomolecular Chemistry, vol. 10, No. 43 (2012), pp. 8660-8668.

Geoffrey C. Hoops et al., "Mechanism-Based Inactivation of tRNA-Guanine Transglycosylase from *Escherichia coli* by 2-Amine-5-(fluoremethyl)pyrrolo[2, 3-d]pyrimidin-4(3H)-one", Biochemistry, vol. 34, No. 47 (1995), pp. 15539-15544.

Miloslave Kverka et al., "Safety and efficacy of the immunosuppressive agent 6-tioguanine in murine model of acute and chronic colitis", BMC Gastroenterology, vol. 11, No. 47 (2011), pp. 1-9.

Alfred C. Liang et al., "Fast-dissolving intraoral drug delivery systems", Expert Opinion on Therapeutic Patents, vol. 11, No. 6, (2001), pp. 951-986.

Camille Mason et al., "Thioguanine for refractory psoriasis: A 4-year experience", Journal of the American Academy of Dermatology, vol. 44, No. 1, (2001), pp. 67-72.

Norihiro Okada et al., "Novel Mechanism of Post-transcriptional Modification of tRNA. Insertion of Bases of Q precursors into tRNA by a specific tRNA transglycosylase reaction", The Journal of Biological Chemistry, vol. 254, No. 8, (1979), pp. 3087-3073.

Sureyya Olgen et al., "Synthesis and Activity of Novel 5-Substituted Pyrrolo[2,3-d] pyrimidine Analogues as $pp60^{0\text{-}Src}$ Tyrosine Kinase Inhibitors", vol. 341, No. 2, (2008), pp. 113-125.

Chandramani Pathak et al., "Queuine promotes antioxidant defence system by activating cellular antioxidant enzyme activities in cancer", Bioscience Reports, vol. 28, No. 2 (2008), pp. 73-81.

C. H. Polman et al., "Drug treatment of multiple sclerosis", BMJ, vol. 321 (2000), pp. 490-494.

Nobuko Shindo-Okada et al., "Transfer Ribonucleic Acid Guanine Transglycosylase Isolated from Rat Liver", Biochemistry, vol. 19, No. 2, (1980), pp. 395-400.

Ingunn M. Stromnes et al., "Active induction of experimental allergic encephalomyelitis", Nature Protocols, vol. 1, No. 4, (2006), pp. 1810-1819.

Sreeja Varhese: "The Queuine-Transfer RNA Pathyway as a novel drug mechanism to treat Multiple Sclerosis", WordCat Thesis/dissertation, (2012), XP002752735, Retrieved from the Internet: URL:http://www.worldcat.org/title/queuine-transfer-rna-pathway-as-a-novel-drug-mechanism-to-treat-multiple-sclerosis/oclc/856580202 [retrieved on Jan. 8, 2016] (2 pages).

Rajan K. Verma et al., "Drug Delivery Technologies and Future Directions", Pharmaceutical Technology On-Line, vol. 25, No. 2 (2001), pp. 1-14.

Palace et al.,"New Treatments and Azathioprine in Multiple Sclerosis," The Lancet, vol. 350, Issue 9073, p. 261, (1997).

Aubrecht et al., "Tissue Specific Toxicities of the Anticancer Drug 6-Thioguanine Is Dependent on the Hprt Status in Transgenic Mice," The Journal of Pharmacology and Experimental Therapeutics, 282(2):1102-1108 (1997).

English Translation of Japanese Office Action for Application No. 2017-516829, dated Jun. 18, 2019, 8 pages.

Robinson et al., "The experimental autoimmune encephalomyelitis (EAE) model of MS: utility for understanding disease pathophysiology and treatment," Handbook of Clinical Neurology 122:173-189 (2014).

French et al., "Queuine, a tRNA anticodon wobble base, maintains the proliferative and pluripotent potential of HL-60 cells in the presence of the differentiating agent 6-thioguanine," Proceedings of the National Academy of Sciences 88: 370-374 (1991).

Chen et al., "Evolution of eukaryal tRNA-guanine transglycosylase: insight gained from the heterocyclic substrate recognition by the wild-type and mutant human and *Escherichia coli* tRNA-guanine transglycosylases," Nucleic Acids Research 39(7):2834 2844(2011).

Johannsson et al., "Crystal Structure of the Human tRNA Guanine Transglycosylase Catalytic Subunit QTRT1," Biomolecules 8(81) (2018).

Joseph, "Why drug makers share their prized compound libraries with competitors," Stat News, Nov. 20, 2015.

\* cited by examiner

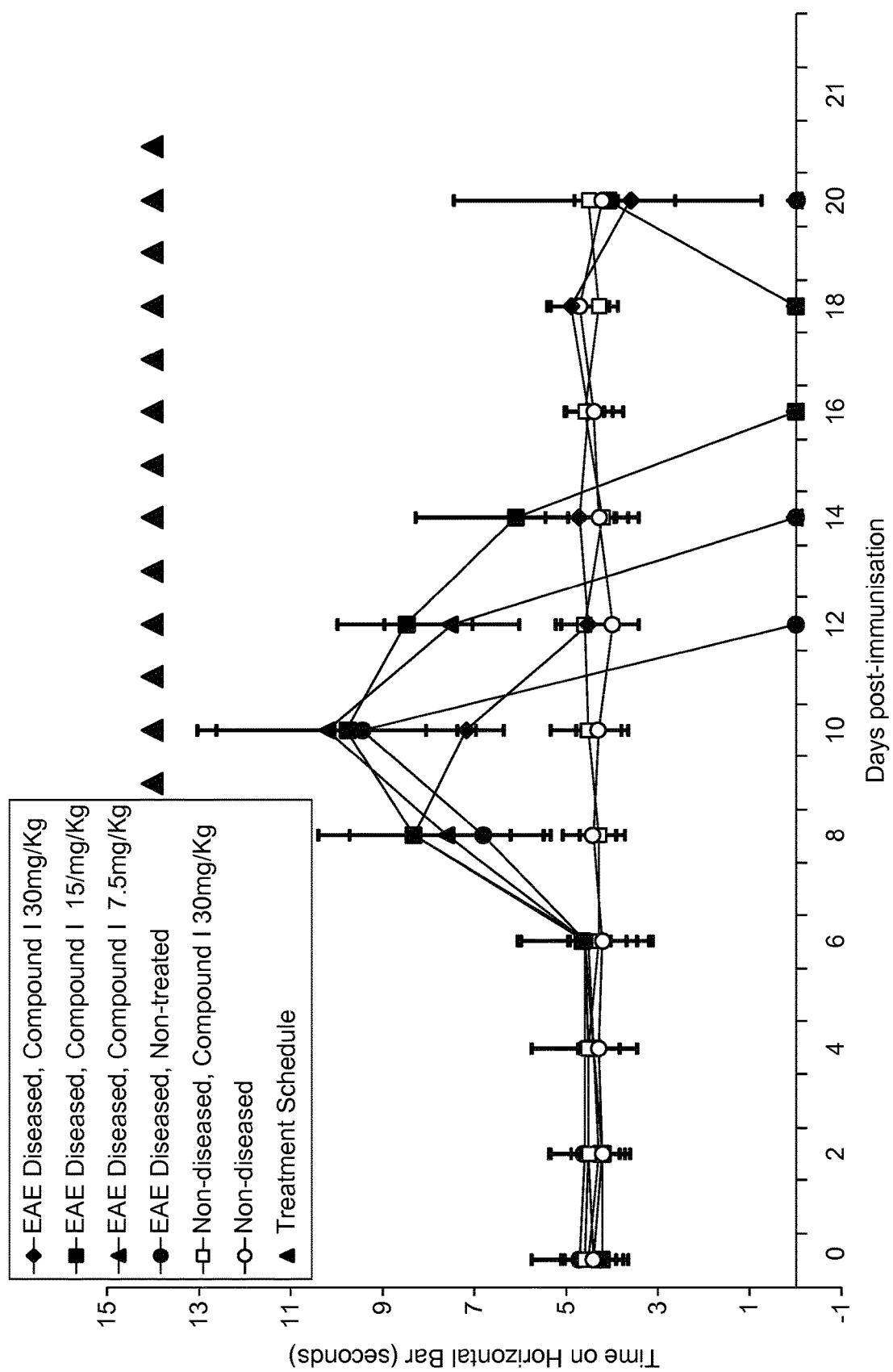

TREATMENTS FOR AUTOIMMUNE DISEASE

TECHNICAL FIELD

The invention relates to a novel approach to the treatment of autoimmune diseases, particularly multiple sclerosis.

BACKGROUND ART

Multiple sclerosis (MS) is a debilitating disease of the central nervous system (CNS) in which the body's own immune system attacks the white matter of the brain and spinal cord. This triggers inflammation-induced damage to the CNS protective myelin layer causing demyelination. Loss of myelin exposes neurons to further attack leading to formation of multiple sclerotic lesions. This damage disrupts the ability of parts of the nervous system to communicate, resulting in a wide range of problems including fatigue, blurred vision, cognitive impairment, and spasticity. Many patients suffer from the development of irreversible motor disability. Long term prognosis is poor, within 15 years of disease onset approximately 50% of patients are unable to walk unassisted (Polman and Uitdehaag, 2000).

MS takes several forms, with new symptoms either occurring in isolated attacks (relapsing forms) or building up over time (progressive forms).

There is at present no known cure for multiple sclerosis. Current treatments attempt to improve function after an attack and/or prevent subsequent attacks.

Medications used to treat MS, while modestly effective, can have adverse effects and be poorly tolerated.

There are a number of injectable front line therapies:
beta interferon 1a (AVONEX®)
beta interferon 1a (REBIF®)
beta interferon 1b (Betaferon)
glatiramer acetate (COPAXONE®)

Interferons may produce flu-like symptoms and some people taking glatiramer experience a post-injection reaction with flushing, chest tightness, heart palpitations, breathlessness, and anxiety, which usually lasts less than thirty minutes. More dangerous but much less common is liver damage. Glatiramer is associated with skin irritation at the site of injection.

Additional therapies include:
Natalizumab which reduces the relapse rate more than first-line agents; however, due to issues of adverse effects such as progressive multifocal leukoencephalopathy it is a second-line agent reserved for those who do not respond to other treatments or with severe disease.
Fingolimod (GILENYA®)—licensed in March 2011 for people with rapidly evolving severe relapsing remitting MS (two or more relapses a year), and as a second line treatment for people whose MS remains active despite treatment with one of the beta interferon drugs.
Dimethyl fumarate (TECFIDERA®) was licensed by the FDA in 2013 and is an oral first line therapy for adults with relapsing remitting forms of MS.
Teriflunomide (AUBAGIO®) was approved by the FDA in September 2012, is an orally available immunomodulatory drug for the treatment of relapsing forms of MS.
Mitoxantrone, whose use is limited by severe adverse effects, systolic dysfunction, infertility, and acute myeloid leukemia is a third-line option for those who do not respond to other medications.

Corticosteroids (or steroids) are sometimes given for a few days, either in the form of tablets or by intravenous drip. While there is no evidence that steroids have any effect on the long-term course of the disease, they can be effective at speeding up recovery from relapse.

No treatment has been shown to change the course of primary progressive MS and as of 2011 only one medication, mitoxantrone, has been approved for secondary progressive MS. In this population, tentative evidence supports mitoxantrone moderately slowing the progression of the disease and decreasing rates of relapse over two years.

There is ongoing research looking for more effective, convenient, and tolerable treatments for relapsing-remitting MS.

Monoclonal antibodies have raised high levels of interest. The CD52 monoclonal antibody alemtuzumab, CD25 monoclonal antibody daclizumab and CD20 monoclonal antibodies such as rituximab, ocrelizumab and ofatumumab have all shown some benefit and are under study as potential treatments. Their use has also been accompanied by the appearance of potentially dangerous adverse effects, most importantly opportunistic infections.

Accordingly, there is a huge unmet medical need for the treatment of MS.

SUMMARY OF THE INVENTION

The present invention provides new medicaments for the treatment of autoimmune diseases, particularly multiple sclerosis.

An imbalance of Th cell function and differentiation can lead to inflammation and autoimmune disease. The activation of naive CD4+ T cells by antigen causes them to differentiate into specialized effector T (Teff) cells (Th1, Th2, or Th17) and into regulatory T (Treg) cells, which suppress the functions of Teff cells, thereby keeping immune responses in check. In particular, Th1 and Th17 cells and their signature cytokines IFN-γ and IL-17 have been shown to play a critical role in the development of many autoimmune diseases, including multiple sclerosis (MS).

A novel mechanism for the regulation of this process and thus treatment of such diseases has been identified. Molecules which can exploit an enzyme complex made of two proteins, tRNA guanine transglycosylase (TGT) also known as queuine tRNA-ribosyltransferase 1, and queuine tRNA-ribosyltransferase domain containing 1 (QTRTD1), subsequently referred to as the queuine-insertase enzyme complex, have been shown to have beneficial effects in models for autoimmune diseases.

Further, those molecules which are selective in avoiding competing pathways, such as not being substrate for Hypoxanthine-guanine phosphoribosyltransferase (HPRT) or, more positively lower interferon gamma levels are particularly efficacious.

The present invention provides new medicaments for the treatment of autoimmune diseases, particularly multiple sclerosis.

BRIEF DESCRIPTION OF THE FIGURES

These and other features, aspects and advantages of the present invention are better understood when the following detailed description of the invention is read with reference to the accompanying drawings, in which:

FIG. 7 depicts motor coordination and hind-limb strength in mice at various time periods post-immunization.

DETAILED DESCRIPTION

Figure 1:
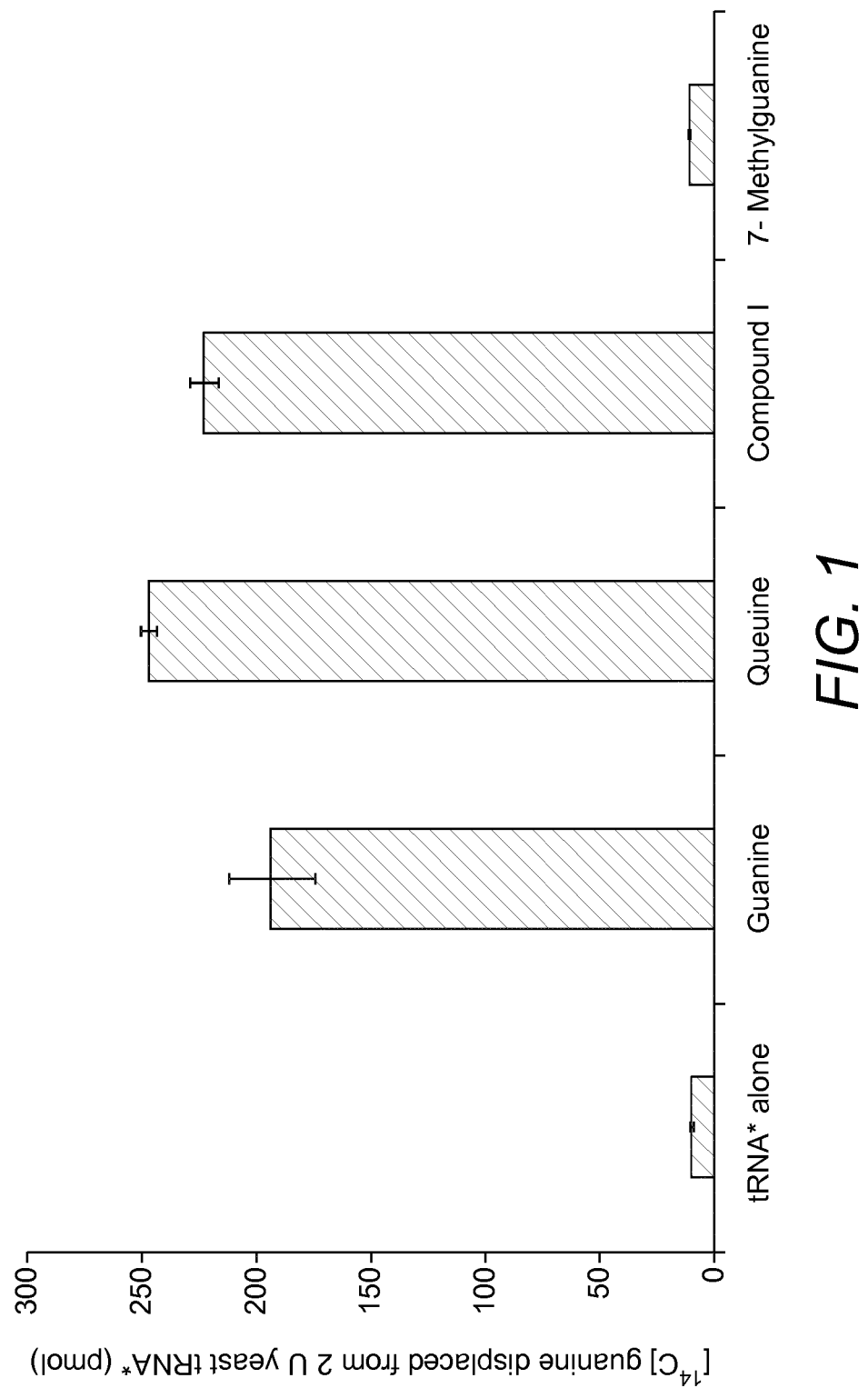
FIG. 1 depicts molecules capable of acting as a queuine-insertase enzyme complex substrate identified by use of a displacement assay.

In a first embodiment it describes a molecule which is capable of acting as substrate for the human queuine-insertase enzyme complex for the treatment of autoimmune disease.

More specifically it describes a molecule capable of acting as substrate for the queuine-insertase enzyme complex for use in the treatment of multiple sclerosis.

In a further embodiment of the invention there is provided a molecule capable of acting as substrate for the queuine-insertase enzyme complex and where said molecule is not a substrate for Hypoxanthine-guanine phosphoribosyltransferase (HPRT) for use in the treatment of autoimmune diseases. Preferably the autoimmune disease is multiple sclerosis.

Additionally described is a molecule capable of acting as substrate for the queuine-insertase enzyme complex, which also has the effect of lowering interferon gamma production in immune cell assays for use in the treatment of autoimmune diseases. Preferably, the autoimmune disease is multiple sclerosis.

In a further embodiment of the invention there is provided a molecule capable of acting as substrate for the queuine-insertase enzyme complex, where said molecule is not a substrate for HPRT and where said molecule has the effect of lowering interferon gamma, for use in the treatment of auto-immune diseases. Preferably the autoimmune disease is multiple sclerosis.

For molecules that lower interferon gamma production in wild-type cells, preferred are those molecules that are able to lower it at a concentration of 100 µM.

Particularly preferred are those molecules which lower interferon gamma to ≤1750 ng/ml.

Most preferred are those molecules which lower interferon gamma to ≤1100 ng/ml.

Alternatively, can test for molecules that lower interferon gamma production by using cells from animals wherein the TGT gene has been knocked out, subsequently referred to as TGT-KO cells). Preferred are those molecules that at a concentration of 100 µM do not lower it ≤3,500 ng/ml.

Particularly preferred are those molecules which do not lower interferon gamma to ≤4250 ng/ml Most preferred are those molecules which do not lower it ≤5000 ng/ml.

The skilled reader will be aware of methods for determining whether or not a particular molecule is a substrate for the queuine-insertase enzyme complex. For example, molecules capable of acting as a queuine-insertase enzyme complex substrate may be identified by use of a displacement assay as described below (FIG. 1):

Production of [8-$^{14}$C] Guanine Labeled tRNA (tRNA*)

Components added in the order listed in Table 1. Before adding the 8-[$^{14}$C] guanine solution to the reaction the solution was neutralised with an equal volume (vol/vol) 0.01 M NaOH, as the [8-$^{14}$C] Guanine is supplied in 0.01 M HCl aqueous solution. A stock solution of yeast tRNA from *Saccharomyces cerevisiae* was made to a concentration of 2 absorbance units (260 nm) in ultrapure nuclease-free water. The recombinant *Escherichia coli* (*E. coli*) tRNA guanine transglycosylase enzyme (*E. coli* TGT) containing an N-terminal polyhistidine tag was produced in BL21 BL21(DE3) tgt:Km$_r$ cells as described previously (Boland et al., 2009).

TABLE 1

Components of [8-$^{14}$C] Guanine tRNA labeling reaction

| Component | Volume (µL) | Final conc. |
| --- | --- | --- |
| 1M Tris-HCl pH 7.5 | 7.5 | 50 mM |
| 5M NaCl | 0.6 | 20 mM |
| 1M MgCl$_2$ | 0.75 | 5 mM |
| 1M DTT | 0.3 | 2 mM |
| Yeast tRNA (2 abs/µl) | 12.5 | 25 Abs total in rxn |
| H$_2$O | to 130 µL | |
| *E. coli* TGT | 10 µL | 10 µg |
| [8-$^{14}$C] guanine | 10 µL | |

The reaction was incubated for 2 h at 37° C. After incubation the reaction was made up to 400 µL with buffer. The reaction mixture was extracted by addition of an of equal volume (400 µL), of Acid Phenol:chloroform (5:1; pH 4.5) and centrifuged at 16,000×g for 5 min. The upper aqueous phase was transferred to a new 1.5 mL tube. The radiolabelled tRNA with [8-$^{14}$C] guanine in the third position of the anticodon loop (tRNA*) was precipitated by the addition of 0.1 volume (40 µL) of 3 M sodium acetate (aq.) and 2 volumes of ethanol (800 µL) and incubated overnight at −20° C. The next morning, the tRNA* was pelleted by centrifugation at 16,000×g for 20 min at 4° C. The pellet was washed with 1 mL of ice-cold 70% ethanol, without disturbing the pellet. The tRNA* pellet was resuspended in 20 µL nuclease-free water and the concentration measured spectrophotometrically at A$_{260}$.

Displacement Assays

Each reaction was set up in triplicate and incubated for 1 h at 37° C. Each of the components in the reaction were added in the order shown in Table 2, with the tRNA* added last to initiate the reaction. 'Compound' refers to the molecules that are under investigation.

TABLE 2

Components of [8-$^{14}$C] guanine displacement assays

| Component | Volume (µL) | Final Concentration |
| --- | --- | --- |
| 1M Tris-HCl pH 7.5 | 7.5 | 50 mM |
| 5M NaCl | 0.6 | 20 mM |
| 1M MgCl$_2$ | 0.75 | 5 mM |
| 1M Dithiothreitol | 0.3 | 2 mM |
| Compound (2 mM stock) | 15 | 200 µM |
| H$_2$O | to 140 | |
| Queuine-insertase enzyme | 10 | 2 µg |
| tRNA* | 2 Abs units | 1.8 µM |

Preparation of the DEAE Columns:

Approximately 25 grams of Whatmann DEAE 52-cellulose resin was weighted into a 50 ml sterile RNA free tube. A volume of 20 ml of 200 mM Tris-HCl pH7.5 was added and the tube inverted 5 times and centrifuged at 750×g in a bench top centrifuge to sediment the resin. The supernatant was removed by pouring and the pH checked. The washing of the resin was repeated another 4 times until the wash reached a pH of 7.5. The resin was suspended in a 1:1 slurry with 200 mM Tris-HCl pH7.5 and loaded into a 1.5 ml spin column (containing a glass fibre filter) until a 1 ml final bed volume of resin was achieved.

After incubation the reaction was loaded onto the column and spun at 0.1×g for 10 seconds. The flow-through was collected and reloaded on the column. This step was repeated 5 times to allow maximum binding of tRNA. The column was then washed with 8×250 μL of Wash Buffer (20 mM Tris-HCl, pH7.5, 10 mM $MgCl_2$, 200 mM NaCl) with 10 second spins at 0.1×g between each wash. These loading and wash steps were collected into scintillation vials. The bound tRNA was then eluted in 4×250 μL aliquots in Elution Buffer (20 mM Tris-HCl, pH7.5, 10 mM $MgCl_2$, 1M NaCl) and collected into scintillation vials. 10 mL of Ecoscint A (scintillation cocktail) was added to all vials. The vials containing the flow-through and washes are counted for displaced [$^{14}$C] guanine.

In this assay (see FIG. 1), maximum displacement by 200 μM queuine base, the natural substrate of the queuine-insertase enzyme complex, is 240 pmol [$^{14}$C] guanine. Background values are ≤10 pmol. Therefore, a displacement of ≥50 pmol is considered a positive substrate for TGT.

Assay for the Ability of Compounds to be Used as Substrates for the Queuine-Insertase Enzyme Complex—by Displacing [$^{14}$C] Guanine from Yeast tRNA (FIG. 1).

Guanine, queuine, N-((2-amino-4-oxo-4,7-dihydro-3H-pyrrolo[2,3-d]pyrimidin-5-yl)methyl)-3-phenylpropan-1-aminium chloride (shown as compound I) and 7-methylguanine were assessed for their ability to replace guanine in yeast tRNA. First, yeast tRNA was charged with [8-$^{14}$C] guanine (tRNA*) by the *E. coli* TGT enzyme. In each reaction 2 $A_{260}$ absorbance units of tRNA* was used along with 200 μM of specified molecule. Reactions were processed on 1 ml DEAE cellulose columns. Reaction flow-through and washes were collected and analysed by liquid scintillation counting for presence of displaced [$^{14}$C] guanine.

Figure 2:
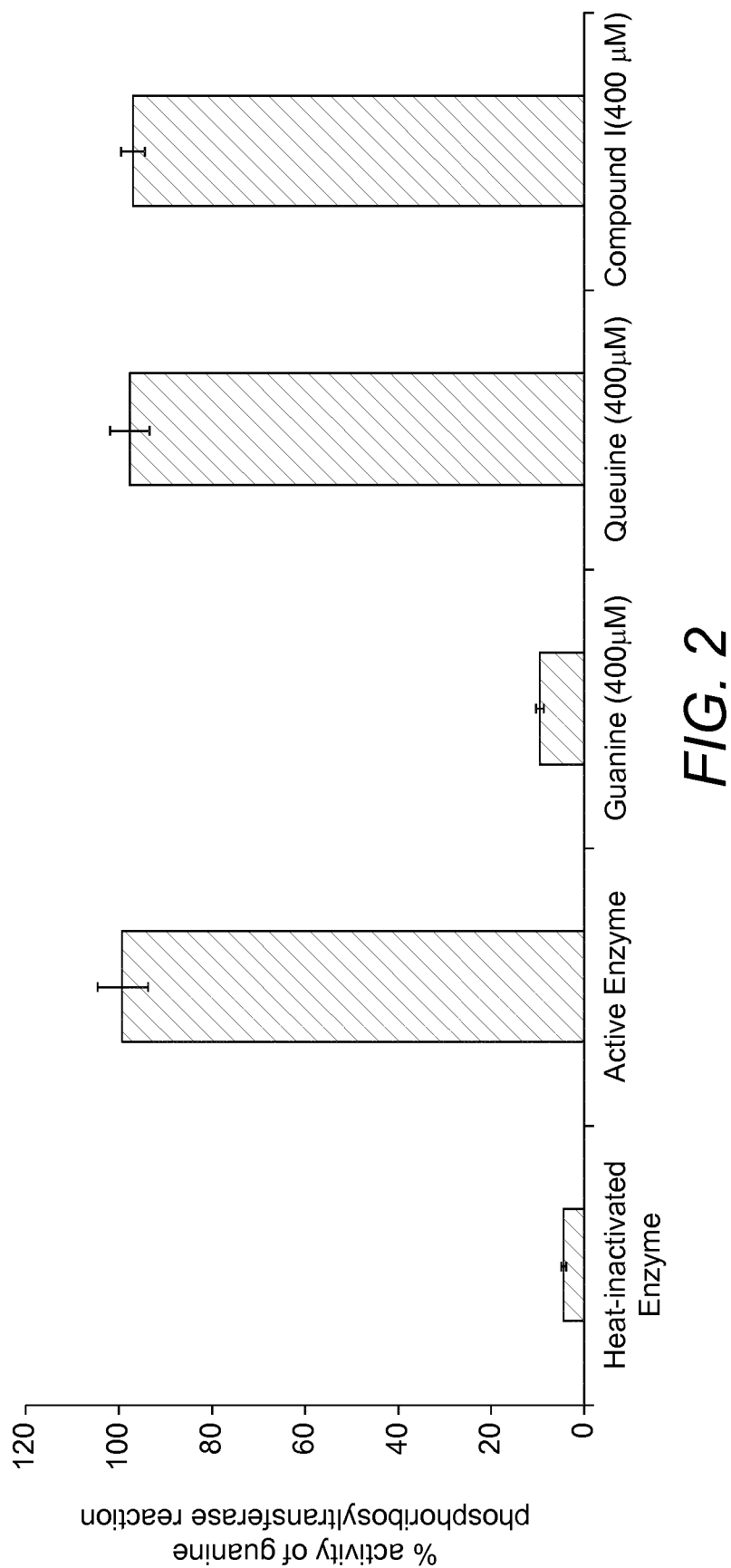
FIG. 2 depicts an assay to evaluate compounds as substrates or inhibitors of the Hypoxanthine-guanine phosphoribosyltransferase enzyme or 'HPRT Assay'.

Similarly, the skilled reader will be aware of methods suitable for determining whether a compound is a substrate or inhibitor of HPRT. For example, molecules that are neither a substrate nor an inhibitor for HPRT may be identified by use of the following assay:

Assay to Evaluate Compounds as Substrates or Inhibitors of the Hypoxanthine-Guanine Phosphoribosyltransferase Enzyme or 'HPRT Assay' (FIG. 2).

Preparation and Equilibration of Column:

Dowex-1×8, mesh size 200-400, was weighed out in a sterile 50 ml tube and washed 3 times with aqueous 1 M HCl to charge the resin. The resin was then washed 5-6 times with (20 mls each) Milli-Q $H_2O$ until a neutral pH was reached. Columns (Bio-rad 10 mL plastic columns) were set up with 1 mL of wet Dowex (wet mix applied, allowed to settle and more applied until a packed volume of 1 mL was reached). The packed resin was rinsed with 10 volumes (v/v) milli-Q $H_2O$ to ensure that a neutral pH and consistent packing was achieved.

HPRT Reactions are set up in 100 μL volume in triplicate with the following components:

20 mM HEPES (pH 8)
10 mM $MgCl_2$
0.1 mM Phosphoribosyl pyrophosphate (PRPP—made fresh on day of assays)
20 μM [8-$^{14}$C]-Guanine
400 μM Compound to be tested The reaction mix was preheated to 37° C. before 10 ng of recombinant human HPRT enzyme was added. Reactions are allowed to proceed for 1 h before being stopped by heating for 8 min at 100° C. A control reaction comprising heat-inactivated enzyme (treated at 100° C. for 8 min prior to adding to the reaction) was also always included.

After inactivation, the reactions were cooled to room temperature (using ice), before being applied to a 1 mL packed resin column of Dowex-1×8, mesh size 200-400. The column was washed with 5 mL milli-Q $H_2O$ and 10 mL 10 mM HCl, to remove unbound, unreacted guanine. GMP was eluted from the column with 5 mL of 50 mM HCl into scintillation vials. 15 mL of scintillation cocktail (Ecoscint A) was added and vials counted to evaluate the level of conversion of [8-$^{14}$C]-guanine to GMP.

For molecules that are neither a HPRT substrate nor an inhibitor, the reaction will yield GMP product in amounts ≥60% of the control reaction containing only [8-$^{14}$C]-guanine.

Results for Guanine, Queuine.HCl (2-Amino-5-[[[(1S,4S,5R)-4,5-dihydroxy-2-cyclopenten-1-yl]amino]methyl]-1,7-dihydro-4H-pyrrolo[2,3-d]pyrimidin-4-one, monohydrochloride) and N-((2-amino-4-oxo-4,7-dihydro-3H-pyrrolo [2,3-d]pyrimidin-5-yl)methyl)-3-phenylpropan-1-aminium chloride (shown as Compound I on graph) are shown in FIG. 2.

Figure 3:
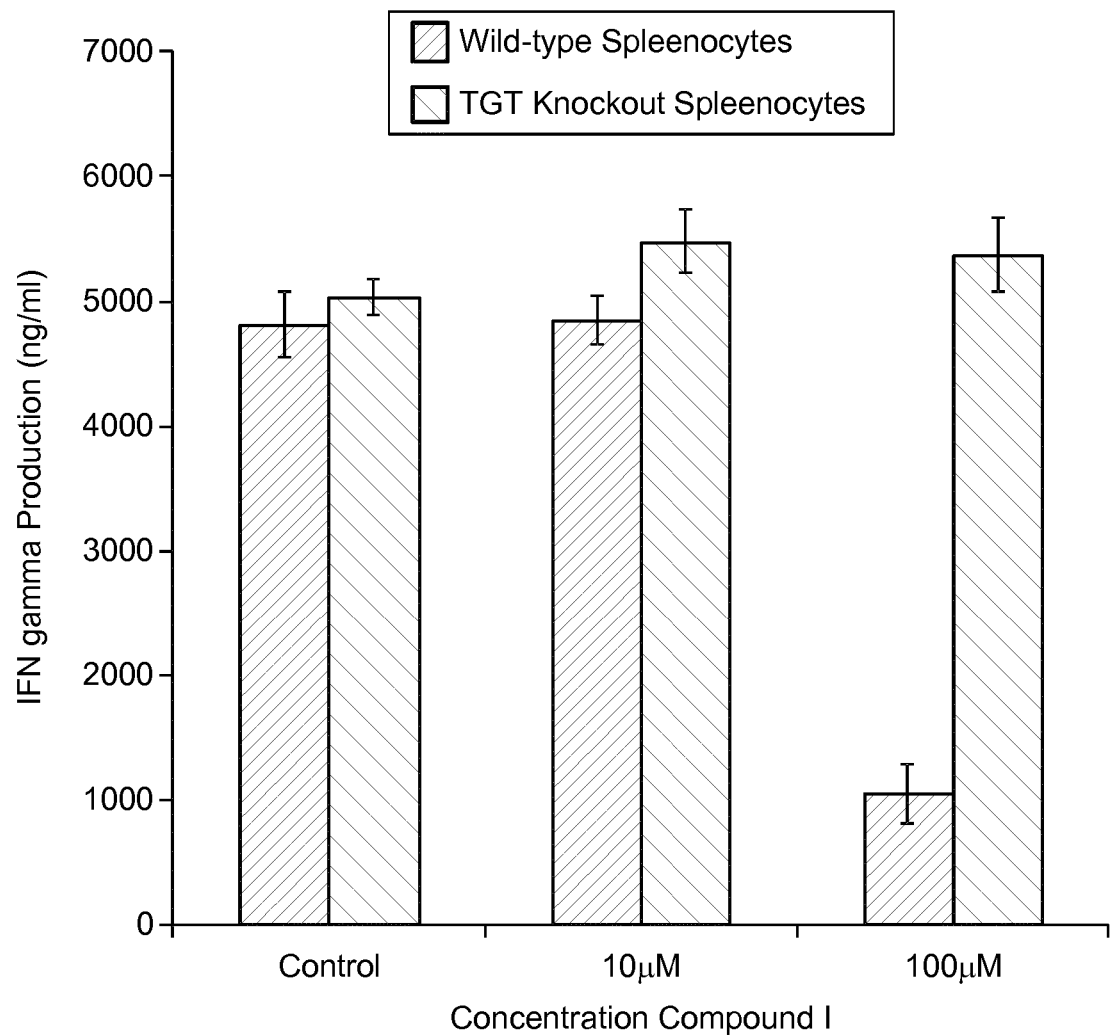
FIG. 3 depicts an ex vivo assay measuring the ability of molecules to lower interferon gamma.
Figure 4A:
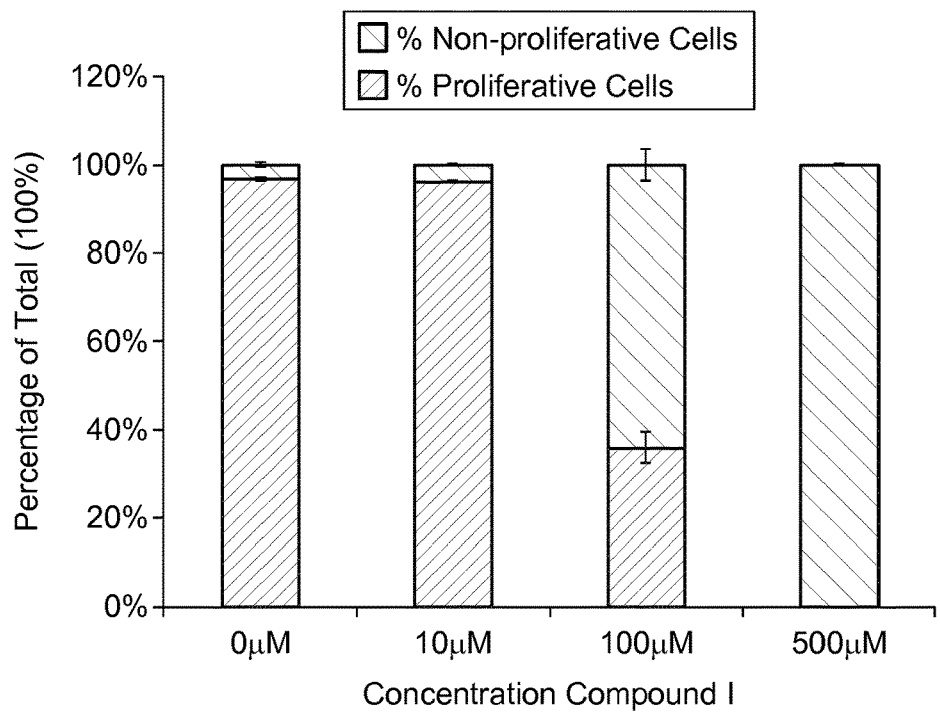
FIGS. 4a, 4b, 4c, and 4d depict the molecules effects on total percentage of proliferation in wild-type spleenocytes, HPRT knockout spleenocytes, HPRT:TGT double knockout spleenocytes, and wild-type versus single TGT knockout spleenocytes respectively.
Figure 4B:
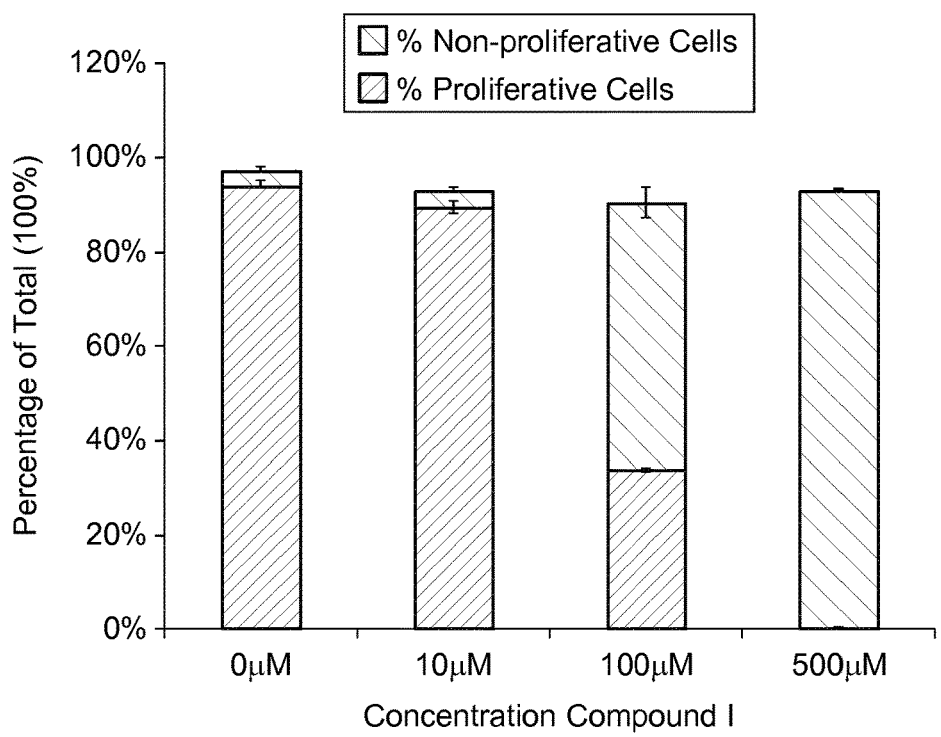
Figure 4C:
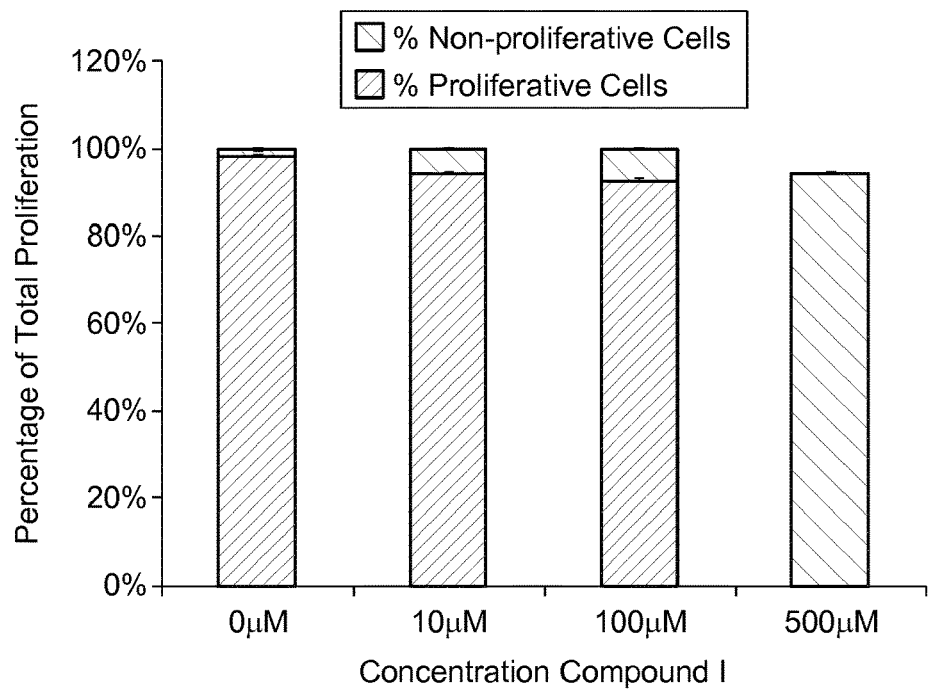
Figure 4D:
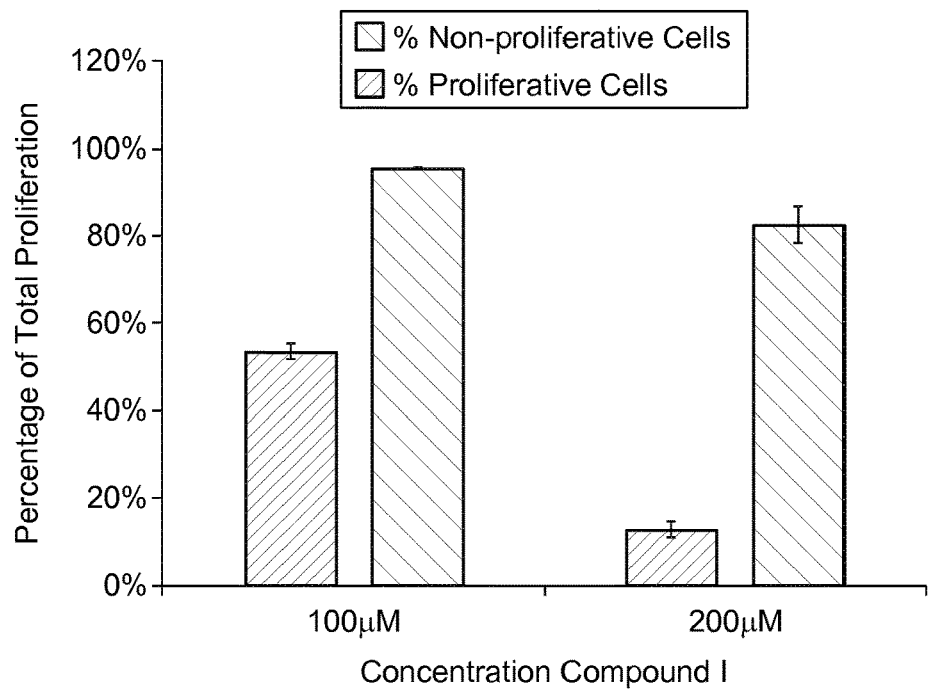

The ability of molecules to lower interferon gamma may be measured with the following ex vivo assay (FIG. 3):

Chronic, monophasic EAE was induced in 8-10 week old female C57BL/6 mice as described by Stromnes and Goverman, (2006). Animals were transcardially perfused with ice-cold phosphate buffered saline (PBS) and the spleen was removed.

Single cell suspensions of spleen were made by extrusion through a 70 micron nylon mesh and the cell washed in cRPMI medium (Roswell Park Memorial Institute media containing 10% fetal bovine serum, 2 mM L-glutamine, 100 units penicillin, 1 mg/ml streptomycin) by centrifugation at 240×g for 5 minutes, counted and seeded at a final density of 1×10$^6$/mL to U-bottomed 96 well plates containing medium alone (negative control) or 100 μl of 50 μg/mL myelin oligodendrocyte glycoprotein peptide ($MOG_{33-55}$). All stock concentrations of molecules were made up in sterile DMSO and tested in cells at 10 μM and 100 μM concentrations. Molecule administrations did not exceed 0.5% final DMSO concentration in cells. After 72 h, the plates were centrifuged at 240×g for 3 minutes to allow the cells to settle down. Supernatants were carefully removed and assayed for IFN gamma according to manufacturer's protocol supplied in the eBioscience ELISA kit.

This test can be used with both wild cells or TGT-KO cells as described herein

Suitable molecules for use in the invention include:
2-amino-5-(((3-phenylpropyl)amino)methyl)-3,7-dihydro-4H-pyrrolo [2,3-d]pyrimidin-4-one
N-((2-amino-4-oxo-4,7-dihydro-3H-pyrrolo[2,3-d]pyrimidin-5-yl)methyl)-3-phenylpropan-1-aminium chloride;
2-amino-5-((butylamino)methyl)-3,7-dihydro-4H-pyrrolo [2,3-d]pyrimidin-4-one N-((2-amino-4-oxo-4,7-dihydro-3H-pyrrolo[2,3-d]pyrimidin-5-yl)methyl)butan-1-aminium chloride 2-amino-5-((hexylamino)methyl)-3,7-dihydro-4H-pyrrolo[2,3-d]pyrimidin-4-one N-((2-amino-4-oxo-4,7-dihydro-3H-pyrrolo[2,3-d]pyrimidin-5-yl)methyl)hexan-1-aminium chloride Queuine; 2-amino-5-((((1S,4S,5R)-4,5-dihydroxycyclopent-2-en-1-yl)amino)methyl)-3,7-dihydro-4H-pyrrolo[2,3-d]pyrimidin-4-one Queuine HCl 2-Amino-5-[[[(1S,4S,5R)-4,5-dihydroxy-2-cyclopenten-1-yl]amino]methyl]-1,7-dihydro-4H-pyrrolo[2,3-d]pyrimidin-4-one, monohydrochloride Without being bound by theory, it appears the compounds of the present invention operate via a new drug pathway. They exploit an enzyme complex made of two proteins: TGT (tRNA guanine transglycosylase) and QTRTD1 (queuine tRNA transglycosylase domain containing 1) herein referred to as the queuine-insertase enzyme complex. The effect is to decrease populations of effector T cells (Teff) and/or increase the relative populations of regulatory T cells (Treg) cells. Treg cells are a part of the immune system that are intricately involved in the determination of self from non-self proteins, i.e., protecting proteins of the self from being attacked by the immune system.

The natural substrate for the queuine-insertase enzyme complex is queuine, a molecule that cannot be synthesised by eukaryotic cells. However, it is readily produced by most bacteria, and in humans queuine must be harvested either from injested food or the gut microflora. The queuine-insertase enzyme complex inserts queuine into the anticodon loop of tyrosyl-, histidinyl-, asparaginyl- and aspartyl-transfer RNA (tRNA of the GUN family; $tRNA_{GUN}$) at the wobble position.

The majority of $tRNA_{GUN}$ in the body is modified at the wobble position with queuine. It is notable that queuine is absent or depleted (hypomodified) in the wobble position of $tRNA_{GUN}$ isotypes in rapidly proliferating cells. Earlier work employing 6-thioguanine (6TG) has shown that use of this alternative substrate for the queuine-insertase enzyme complex can have a dramatic effect on the murine model of chronic MS (i.e. Experimental Autoimmune Encephalomyelitis; EAE). Unfortunately, from a therapeutic perspective, 6TG suffers from the problem that it is a more potent substrate for HPRT (approx. 10 fold higher than for the queuine-insertase enzyme complex). It is subsequently incorporated into DNA, making it genotoxic and unsuitable as a treatment for MS.

The present invention revolves around molecules able to exploit the beneficial aspects of 6TG (queuine-insertase dependent exchange into the wobble position of $tRNA_{GUN}$), but which circumvent the problem associated with 6TGs' main biological activity (i.e. HPRT activity and subsequent insertion into DNA).

FIGS. 4a-4d show that proliferation was reduced to less than 50% in wild-type T cells upon treatment with N-((2-amino-4-oxo-4,7-dihydro-3H-pyrrolo[2,3-d]pyrimidin-5-yl)methyl)-3-phenylpropan-1-aminium chloride at 100 µM concentration (shown as Compound I in FIG. 4a-d). Lack of HPRT involvement in the observed effect was demonstrated by a similar reduction of proliferation of cells in which the HPRT gene had been knocked out (HPRT KO, FIG. 4b). Lack of HPRT activity has also been confirmed by in vitro assay employing recombinant HPRT enzyme wherein the molecule is shown not to be a substrate or inhibitor (FIG. 2). The requirement for the queuine-insertase enzyme complex is confirmed by the lack of effect of N-((2-amino-4-oxo-4,7-dihydro-3H-pyrrolo[2,3-d]pyrimidin-5-yl)methyl)-3-phenylpropan-1-aminium chloride (shown as Compound I) at 100 µM concentration on on proliferation in cells in which the TGT gene has been knocked out (TGT KO, FIG. 4d). These data indicate that the mechanism of action is indeed mediated by the queuine-insertase enzyme complex, which is further confirmed (FIG. 4c) by the fact that the double TGT:HRRT knockout is essentially unaffected when treated with N-((2-amino-4-oxo-4,7-dihydro-3H-pyrrolo[2,3-d]pyrimidin-5-yl)methyl)-3-phenylpropan-1-aminium chloride (Formula I) at 100 µM concentration. In vitro analysis of N-((2-amino-4-oxo-4,7-dihydro-3H-pyrrolo[2,3-d]pyrimidin-5-yl)methyl)-3-phenylpropan-1-aminium chloride (Compound I) using recombinant TGT enzyme has also shown that the compound is a substrate for TGT (FIG. 1). The data demonstrates that said compound operates as a substrate for the queuine-insertase enzyme complex—but is not a substrate for HPRT.

The substrate of the queuine-insertase enzyme complex functions to suppress encepholitogenic effector and memory T cell populations without impacting the naïve population. These same immune cell populations broadly contribute to the pathogenesis of all autoimmune diseases.

The transfer RNA (tRNA) of rapidly proliferating cells is deficient (hypomodified) in queuine modification; examples include foetal liver, multiple tumour types and regenerating adult liver. By contrast, the tRNA of adult, fully differentiated cells contains high levels of queuine, which cannot be displaced once incorporated.

It could be expected that the tRNA of rapidly expanding immune cells (as occurs in an autoimmune response) are likewise deficient in the queuine modification. Incorporation of novel Queuine Insertase substrates selectively into the queuine-deficient tRNA of immune cells could disrupt proliferation and cytokine production thereby modulating the immune response.

Compounds of the present invention find utility in the treatment of auto-immune conditions, including but not limited to multiple sclerosis, rheumatoid arthritis, ulcerative colitis, psoriasis, diabetes and inflammatory bowel disease, including Crohn's disease; and as agents to suppress transplant rejection.

The invention also relates to a method of treating multiple sclerosis in a mammal, particularly a human, comprising administering to said mammal an amount of a molecule as defined herein, or a pharmaceutically acceptable salt or solvate thereof.

The term 'treatment' is intended to include curing, reversing, alleviating, palliative and prophylactic treatment of the condition.

The invention further relates to molecules of the invention in combination with other suitable agents, for use in the treatment multiple sclerosis.

Patients suffering from multiple sclerosis are commonly co-administered additional therapeutic agents. For patients suffering a severe attack, intravenous corticosteroids, such as methylprednisolone or techniques such as or plasmapheresis may be coadministered with any treatment.

The effects of nerve cell damage caused by multiple sclerosis result in diverse forms of damage to the patient. Nerve damage can lead to pain, difficulty with control of bladder and many other issues. For this reason, additional medicaments are often prescribed patients with multiple sclerosis to help treat the effects of MS damage. Suitable co-administrants would include:

For Bladder Problems
    botulinum toxin (Botox)
    desmopressin (Desmospray, Desmotabs)
    oxybutynin (Ditropan, Lyrinel)
    tolterodine (Detrusitol)

For Depression
   amitriptyline (Triptafen)
   fluoxetine (Prozac)
   imipramine (Tofranil)
   paroxetine (Seroxat)
For Erectile Dysfunction
   alprostadil (Caverject, MUSE, Viridal Duo)
   sildenafil citrate (Viagra)
   tadalafil (Cialis)
   vardenafil (Levitra)
For Fatigue
   amantadine (Lysovir, Symmetrel)
   modafinil (Provigil)
For Optic Neuritis
   steroids
For Pain
   amitriptyline (Triptafen)
   carbamazepine (Tegretol)
   gabapentin (Neurontin)
   ibuprofen
   imipramine (Tofranil)
   lamotrigine (Lamictal)
   phenytoin (Epanutim)
   pregabalin (Lyrica)
For Problems with Walking
   fampridine (Fampyra)
For Psuedobulbar Affect
   Nuedexta
For Spasticity and Spasms
   baclofen (Lioresal)
   botulinum toxin (Botox)
   carbamazepine (Tegretol)
   clonazepam (Rivotril)
   dantrolene (Dantrium)
   diazepam (Valium)
   gabapentin (Neurontin)
   phenol
   Tetrahydrocannabinol and cannabidiol (Sativex)
   tizanidine (Zanaflex)
For Tremor
   clonazepam (Rivotril)
   thalamotomy
For Trigeminal Neuralgia
   carbamazepine (Tegretol)
   gabapentin (Neurontin)
   oxcarbazepine (Trileptal)
   phenytoin (Epanutim)
   pregabalin (Lyrica)

Other therapeutic agents are commonly administered to patients with MS. Other such medicaments are well known to physicians and others skilled in therapy.

Such agents may be administered sequentially, simultaneously or concomitantly.

The invention also relates to a pharmaceutical composition comprising a molecule of the present invention and a pharmaceutically acceptable diluent or carrier.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Compounds of formula (I) may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (I) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of formula (I) may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques.

Compounds of the invention may also be administered topically to the skin or mucosa, that is, dermally or transdermally.

The compounds of formula (I) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. For intranasal use, the powder may comprise a bioadhesive agent, for example, chitosan or cyclodextrin.

The pressurised container, pump, spray, atomizer, or nebuliser contains a solution or suspension of the compound of formula (I) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (I) may also be administered directly to the eye or ear, typically in the form of drops of a micronised suspension or solution in isotonic, pH-adjusted, sterile saline.

Compounds of formula (I) may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO-A-91/11172, WO-A-94/02518 and WO-A-98/55148

EXPERIMENTAL

The synthesis of various molecules suitable for use in the present invention are described below.

All starting materials and reagents are commercially available and were obtained from Aldrich with exception of 2-amino-3H-pyrrolo[2,3-d]pyrimidin-4(7H)-one which was purchased from Fluorochem.

Preparation 1: 2-octanoylamino-pyrrolo[2,3-d]pyrimidin-4-one

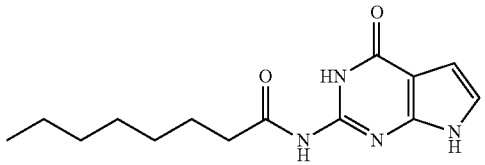 [SMILES: CCCCCCCC(=O)Nc1nc2[nH]ccc2c(=O)[nH]1]

A 50 cm³ round-bottomed flask containing a stirring bar was charged with 2-amino-3H-pyrrolo[2,3-d]pyrimidin-4 (7H)-one (2.00 g, 13.33 mmol). The flask was fitted with a septum and placed under an Ar atmosphere. Freshly distilled pyridine (20.00 cm³) was added via syringe and the resulting suspension cooled on ice. The solution was allowed to equilibrate at this temperature (ca. 5 min) and then octanoyl chloride (6.80 cm³, 39.99 mmol) was added dropwise. The resulting suspension was heated at 85° C. for 30 min. After cooling to room temperature 6.5% ethanolic ammonia (60 cm³) was added and the resulting suspension stirred at room temperature overnight. The precipitate of product was removed via vacuum filtration and washed with ethanol followed by diethyl ether to yield the desired product (2.56 g, 70%) pure as a yellow solid, m.p.>300° C. (decomposition). Procedure based on Akimoto et al. 1986 and Akimoto et al. 1988

$\delta_H$ (400 MHz, DMSO-$d_6$):
0.86 (3H, t, J 5.1), 1.26 (8H, m), 1.58 (2H, app. quintet), 2.01 (1H, br s, NH), 2.43 (2H, t, 3 5.1), 6.40 (1H, d, J 2.0), 7.01 (1H, d, J 2.0), 11.43 (1H, br s, NH), 11.67 (1H, br s, NH)

HRMS (m/z ESI'):
Found: 275.1517 ([M-H]' $C_{14}H_{19}N_4O_2$; Requires: 275.1508)

Preparation 2: 2-octanoylamino-5-((dibenzyl)amino) methyl)-pyrrolo[2,3-d]pyrimidin-4-one

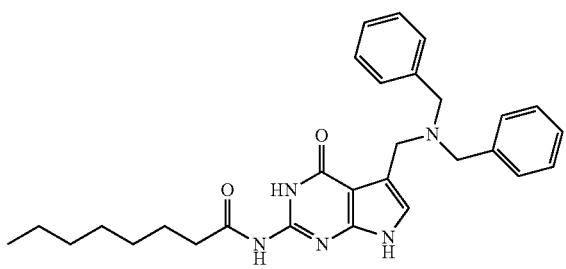 [SMILES: CCCCCCCC(=O)Nc1nc2[nH]cc(CN(Cc3ccccc3)Cc3ccccc3)c2c(=O)[nH]1]

A 50 cm³ reaction vessel containing a stirring bar was charged with 2-octanoylamino-pyrrolo[2,3-d]pyrimidin-4-one (1.00 g, 3.60 mmol), dibenzylamine (2.00 cm³, 10.80 mmol), formalin (349.00 μL, 12.60 mmol) and 80% aqueous acetic acid (36 cm³). The resulting suspension was heated at 60° C. for 20 h, cooled to room temperature, diluted with 0.5 M HCl (36 cm³) and stirred at room temperature for 30 min. The mixture was neutralised with conc. aq. ammonia (36 cm³) and extracted with chloroform (3×50 cm³). The organic extracts were combined, dried (MgSO₄) and evaporated to dryness. The crude residue was purified by column chromatography (9:1 dichloromethane-MeOH-7:3 dichloromethane-MeOH) to give the desired compound (1.45 g, 84%) as a yellow powder m.p.>300° C. (decomposition). Procedure based on Akimoto et al. 1986 and Akimoto et al. 1988

$\delta_H$ (400 MHz, DMSO-$d_6$):
0.86 (3H, t, J 7.1), 1.25 (8H, m), 1.57 (2H, m) 2.42 (2H, t, J 7.1), 3.57 (4H, s), 3.76 (2H, s), 6.88 (1H, S), 7.23 (2H, t, J 7.3), 7.31 (4H, app. t), 7.41 (4H, d, J 7.3), 11.34 (1H, s, NH), 11.57 (1H, s, NH), 11.68 (1H, S, NH)

HRMS (m/z ESI⁺):
Found: 486.2863 ([M+H]⁺$C_{29}H_{36}N_5O_2$; requires: 486.2869)

Example 1: 2-amino-5-(((3-phenylpropyl)amino) methyl)pyrrolo[2,3-d]pyrimidin-4-one

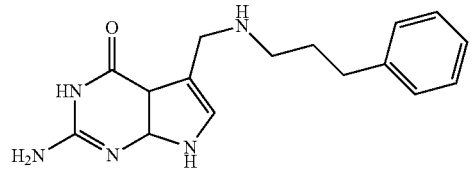 [SMILES: NC1=NC2NC=C(CNCCCc3ccccc3)C2C(=O)N1]

A large carousel tube containing a stirring bar was charged with 2-octanoylamino-5-((dibenzyl)amino)methyl)-pyrrolo[2,3-d]pyrimidin-4-one (100.0 mg, 0.21 mmol), 3-phenylpropylamine (146.00 μL, 1.03 mmol) and 1:1 THF-methanol (2.00 cm³). The suspension was degassed and the reaction vessel sealed. The suspension was heated at 75° C. for 24 h, cooled to room temperature and treated with 5 M KOH (146.00 μL) and stirred at room temperature for 65 h. The solution was concentrated in vacuo and the crude residue purified by column chromatography (9:0.9:0.1 dichloromethane-MeOH—NH₄OH). The resulting solid was washed with HPLC grade hexane followed by diethyl ether in order to remove trace impurities. This gave the desired compound (28 mg, 46%) as an orange powder, m.p.>300° C. (decomposition). Procedure based on Akimoto et al. 1986 and Akimoto et al. 1988

$\delta_H$ (600 MHz, DMSO-$d_6$):
1.24 (1H, br s, NH), 1.66 (2H, app. quintet,), 1.91 (1H, s, NH), 2.44 (2H, t, J 6.9,), 2.57 (2H, t, J 6.9,), 3.59 (2H, s,), 6.15 (2H, br s,), 6.45 (1H, s,), 7.15 (1H, t, J 7.4,), 7.16 (3H, m), 7.25 (2H, app. t,), 10.70 (1H, br s)

δc (600 MHz, DMSO-$d_6$):
30.6, 32.9, 45.2, 47.5, 48.6, 79.2, 98.7 (q), 113.6 (q), 125.5, 128.2, 128.3, 142.3 (q), 152.2 (q), 160.5 (C=O)

$v_{max}$ (film)/cm⁻¹:
697, 748, 749, 1080, 1420, 1596, 2927

HRMS (m/z ESI⁺):
Found: 298.1662 ([M+H]⁺$C_{16}H_{20}N_5O$; Requires: 298.1668)

Preparation 3: 2-chloro-3-oxopropanenitrile

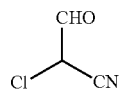

In a dry round bottomed flask under a positive pressure of argon, a suspension of NaOMe (7.14 g, 0.13 mol) in dry THF (90 mL) was cooled to −5° C. Methyl formate (9 mL, 0.15 mol) was added dropwise over 1 min by syringe and stirring was continued at −5° C. for 20 min. Then chloroacetonitrile (8.33 mL, 0.13 mol) was added dropwise via a dropping funnel over 45 min. The mixture turned from white to yellow and was stirred for a further 2 h at −5° C. at which point the reaction mixture was orange. The bath was removed and the reaction was allowed to warm up to room temperature. An aliquot of the reaction mixture was treated with a drop of concentrated HCl and analysed by TLC which indicated the presence of the desired product with an $R_f$=0.45, eluting with 100% EtOAc. The mixture was cooled to 0° C. and concentrated HCl (12 mL) was added dropwise during which time the mixture reaction became cherry-red. The resultant suspension was filtered through a pad of celite, and the celite was washed with EtOAc until the filtrate became colourless. The collected filtrates were concentrated at reduced pressure with the water bath at a temperature no higher than 40° C. to afford chloro(formyl)acetonitrile[1] as a black oil, in quantitative yield, which was used without further purification. Procedure based on Brooks 2012.

$\delta_H$ (400 MHz, CDCl$_3$) 9.38 (s, 1H).

$\delta_C$ NMR (400 MHz, DMSO-d$_6$) δ 168.2, 126.6, 67.8.

Preparation 4: 2-amino-4,7-dihydro-4-oxo-3H-pyrrolo[2,3-d]pyrimidine-5-carbonitrile

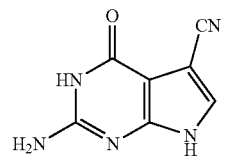 [SMILES: N#Cc1c[nH]c2nc(N)[nH]c(=O)c12]

2,4-Diamino-6-hydroxypyrimidine (3.00 g, 24 mmol) was added to a solution of sodium acetate (6.4 g, 76 mmol) in millipore water (90 mL) and stirred at 50° C. for 1 hour. While still at 50° C. a solution of crude chloro(formyl)acetonitrile (3.00 g, 32 mmol) in mQ water (44 mL) was added dropwise with a dropping funnel, during which time the reaction turned beigeand heating continued for 18 h at 50° C., after which time the reaction was heated to 100° C. for 3 h. The reaction mixture was allowed to cool to room temperature and the solid removed by filtration. The solid was suspended in EtOH and 5M aqueous KOH solution was added until the solid dissolved. Charcoal was added to the solution and the mixture stirred for 30 minutes before removal of the solid by filtration. The pH of the filtrate was adjusted to pH=6 with concentrated aqueous HCl solution during which time a precipitate formed and was collected by filtration. In order to remove the final traces of water from the solid it was dissolved in a mixture of toluene/methanol 1/1 and then concentrated at reduced pressure. The resultant solid was dried over P$_2$O$_5$ to afford the desired compound (1.68 g, 9.6 mmol, 40% yield) as beige solid. Procedure based on Brooks 2012.

$\delta_H$ (400 MHz, DMSO-d$_6$) δ 11.98 (br s, 1H) 10.74 (br s, 1H), 7.59 (s, 1H), 6.43 (s, 2H).

$\delta_C$ (100 MHz, DMSO-d$_6$) δ 158.0, 154.3, 152.1, 128.2, 116.4, 99.2, 86.0.

HRMS (m/z ESI$^-$): C$_7$H$_5$N$_5$O [M−H]$^-$ Found 174.0415 Requires: 174.0416.

Preparation 5: 4,7-Dihydro-4-oxo-2-[(triphenylmethyl)amino]-3H-pyrrolo[2,3-d]pyrimidine-5-carbonitrile

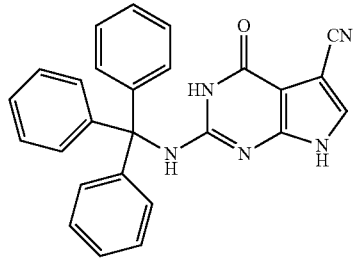 [SMILES: N#Cc1c[nH]c2nc(NC(c3ccccc3)(c3ccccc3)c3ccccc3)[nH]c(=O)c12]

In a dry round bottomed flask under an atmosphere of argon, trityl chloride (1.20 g, 4.28 mmol) was added to a solution of 2-amino-4,7-dihydro-4-oxo-3H-pyrrolo[2,3-d]pyrimidine-5-carbonitrile (0.50 g, 2.85 mmol) in dry pyridine (29 mL). The mixture reaction was heated at 90° C. for 48 h. The reaction mixture was concentrated under reduced pressure then absorbed on silica gel and purified by flash chromatography on silica gel eluting with dichloromethane/MeOH with a gradient starting at 2% of MeOH and rising to 10%. The desired compound was obtained as a brown solid (0.63 g, 1.5 mmol, 53% yield).

Procedure based on Ölgen 2008.

$\delta_H$ (400 MHz, DMSO-d$_6$) δ 11.80 (br s, 1H); 10.64 (br s, 1H), 7.56 (s, 1H), 7.41 (s, 1H), 7.29-7.28 (m, 12H), 7.23-7.17 (m, 3H), 5.73 (s, 1H).

HRMS (m/z ESI$^+$): C$_{26}$H$_{18}$N$_5$O [M−H]$^+$ Found 416.1514 Requires: 416.1511.

Preparation 6: 4,7-Dihydro-4-oxo-2-[(triphenylmethyl)amino]-3H-pyrrolo[2,3-d]pyrimidine-5-carboxaldehyde

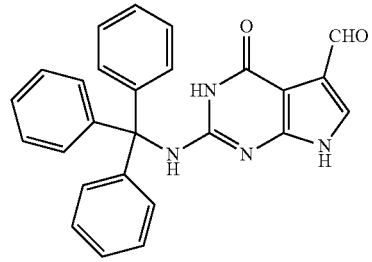 [SMILES: O=Cc1c[nH]c2nc(NC(c3ccccc3)(c3ccccc3)c3ccccc3)[nH]c(=O)c12]

HMDS (6 mmol, 1.3 mL) was added to a mixture of 4,7-dihydro-4-oxo-2-[(triphenylmethyl)amino]-3H-pyrrolo[2,3-d]pyrimidine-5-carbonitrile (1.30 g, 3 mmol) with ammonium sulphate (397 mg, 0.3 mmol) in dry toluene (8 mL) in a round bottomed flask. A reflux condenser was fitted, and the flask was heated at reflux temperature overnight. The mixture was cooled to room temperature and concentrated under reduced pressure. Under a positive pressure of argon, the crude reaction mixture was solubilised in dry dichloromethane (8 mL) and cooled to −78° C. At this temperature, DiBAL-H (4.5 mL, 1 M in dichloromethane, 4.5 mmol) was added dropwise. After 2 hours, analysis by TLC (EtOAc 100%) indicated that some starting material remained. So, a further 2 mL DiBAL-H solution was added dropwise. After 1 hour, the reaction was complete and a mixture of H$_2$O/AcOH (9/1, 3.5 mL) was added at −78° C. The reaction mixture was allowed to warm to room temperature slowly. A mixture of EtOAc/H$_2$O (1/1, 300 mL) was added to the reaction mixture and stirring continued at room temperature for 2 hours. The layers were separated and the organic layer was washed with brine and the aqueous layers were extracted with EtOAc. The combined organic fractions were dried over MgSO$_4$, filtered and concentrated at reduced pressure. The crude reaction product was filtered through a pad of silica gel eluting with EtOAc to afford a yellow solid (1.01 g, 2.38 mmol, 76%). Procedure based on Brooks 2010 and Brooks 2012.

$\delta_H$ (400 MHz, DMSO-d$_6$) δ 11.82 (s, 1H), 10.63 (s, 1H), 9.99 (s, 1H), 7.54 (s, 1H), 7.31-7.27 (m, 13H), 7.23-7.19 (m, 3H).

HRMS (m/z ESI$^-$): C$_{26}$H$_{18}$N$_4$O$_2$ [M−H]$^-$ Found 419.1508 Requires: 419.1508.

Preparation 7: 5-((3-phenylpropylamino)methyl)-2-(tritylamino)-3H-pyrrolo[2,3-d]pyrimidin-4(7H)-one

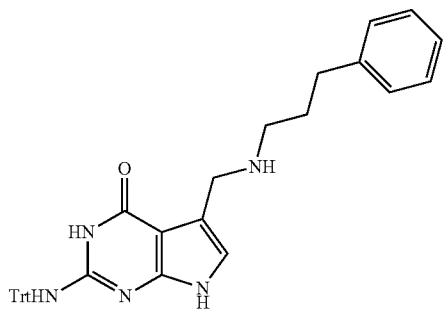

General Procedure A:

To a suspension of N-((4-oxo-2-(tritylamino)-4,7-dihydro-3H-pyrrolo[2,3-d]pyrimidin-5-yl)methyl)formamide (200.0 mg, 0.48 mmol) and sodium sulphate (5.0 mg) in methanol (5 cm$^3$) under an argon atmosphere was added 3-phenylpropylamine (74.00 μL, 0.52 mmol) and the resulting suspension stirred at room temperature for 2 h. Sodium borohydride (55.00 mg, 1.43 mmol) was then added and the reaction mixture stirred at room temperature for a further 1 h. Water (5 cm$^3$) was added and the resulting suspension stirred for 10 min before being extracted with dichloromethane (3×5 cm$^3$). The combined organic layers were dried (MgSO$_4$) and concentrated in vacuo to yield the crude product which was purified by flash chromatography (9:1 dichloromethane-MeOH) to yield the desired compound as a white solid (210 mg, 41.8%), m.p.>300° C. (decomposition). Procedure based on Brooks 2010 and Brooks 2012.

$^1$H (400 MHz, DMSO-d$_6$): 1.73 (2H, quintet, J 7.8), 2.56 (4H, m), 3.74 (1H, s), 6.42 (1H, s, H-6), 7.19 (20H, m), 7.45 (1H, bs, NH), 10.78 (1H, bs, NH)

$^{13}$C (400 MHz, DMSO-d$_6$): 31.7, 32.8, 45.4, 47.8, 70.4 (q), 99.7 (q), 114.9, 117.6 (q), 125.9, 126.0, 126.9, 128.0, 128.6, 129.0, 142.6 (q), 145.4 (q), 150.0 (q), 150.4 (q), 159.7 (C=O)

HRMS (m/z—ESI$^+$): Found: 540.2757 [M+H]$^+$ C$_{35}$H$_{34}$N$_5$O Requires: 540.2765).

$v_{max}$/cm$^{-1}$: 1542, 1611, 1670, 2868, 2951

Example 2: N-((2-amino-4-oxo-4,7-dihydro-3H-pyrrolo[2,3-d]pyrimidin-5-yl)methyl)-3-phenylpropan-1-aminium chloride

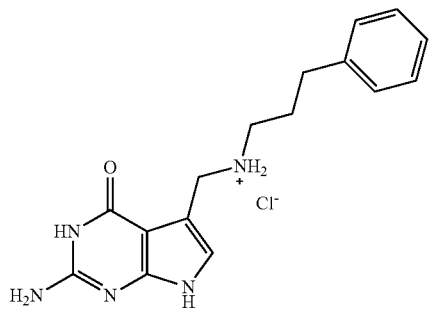 [SMILES: Nc1nc2[nH]cc(C[NH2+]CCCc3ccccc3)c2c(=O)[nH]1 ; [Cl-]]

General Procedure B:

A 5 cm$^3$ reaction vessel containing a stirring bar was charged with 5-((3-phenylpropylamino)methyl)-2-(tritylamino)-3H-pyrrolo[2,3-d]pyrimidin-4(7H)-one (210.0 mg, 0.39 mmol) and 1.25 M methanolic HCl (3 cm$^3$). The resulting solution was stirred at room temperature for 16 h. The precipitated product was removed by vacuum filtration and washed with dichloromethane to yield the desired compound as a white powder (84 mg, 68%), m.p.>300° C. (decomposition). Procedure based on Brooks 2010 and Brooks 2012.

$\delta_H$ (600 MHz, DMSO-d$_6$):
1.90 (2H, app. quintet), 2.63 (2H, t, J 7.8), 2.90 (2H, m), 4.13 (2H, t, J 5.2), 6.57 (2H, bs), 6.80 (1H, d, J 2.3), 7.16 (3H, m), 7.26 (2H, t, J 7.0), 9.11 (2H, bs), 11.05 (1H, m, NH), 11.31 (1H, broad doublet, NH)

$\delta_C$ (125 MHz, DMSO-d$_6$):
27.6, 32.1, 42.9, 45.6, 48.9, 98.6, 108.7 (q), 117.9 (q), 126.4, 128.6, 128.7, 140.9 (q), 152.9 (q), 160.5 (C=O)

HRMS (m/z ESI$^+$): Found: 298.1662 (M$^+$C$_{16}$H$_{20}$N$_5$O Requires: 298.1664)

$v_{max}$ (film)/cm$^{-1}$: 1456, 1625, 2443, 2713, 2756, 2873, 2933, 3184

Preparation 8 5-((3-butylamino)methyl)-2-(tritylamino)-3H-pyrrolo[2,3-d]pyrimidin-4(7H)-one

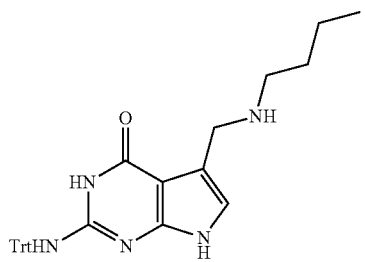

Prepared as per general procedure A using N-((4-oxo-2-(tritylamino)-4,7-dihydro-3H-pyrrolo[2,3-d]pyrimidin-5-yl) methyl)formamide (200.00 mg, 0.48 mmol), n-butylamine (95.00 μL, 0.95 mmol) and NaBH$_4$ (55 mg, 1.43 mmol) to yield the desired product as a white powder (200 mg, 88%), m.p.>300° C. (decomposition).

$\delta_H$ (400 MHz, DMSO-$d_6$):
0.84 (3H, t, J 7.3), 1.30 (2H, app. sextet), 1.51 (2H, app. quintet), 2.82 (2H, t, J 7.3), 4.01 (2H, s), 6.62 (1H, s), 7.24 (15H, m), 7.57 (1H, bs), 11.07 (1H, bs)

$\delta_C$ (400 MHz, DMSO-$d_6$):
13.9, 19.6, 28.0, 42.9, 46.0, , 70.6 (q), 99.4 (q), 108.9, 118.0 (q), 127.0, 128.1, 129.0, 145.2 (q), 150.5 (q), 150.6 (q), 160.3 (C=O)

$v_{max}$ (film)/cm$^{-1}$:
1545, 1613, 1672, 2870, 2956

Example 3 N-((2-amino-4-oxo-4,7-dihydro-3H-pyrrolo[2,3-d]pyrimidin-5-yl)methyl)butan-1-aminium chloride

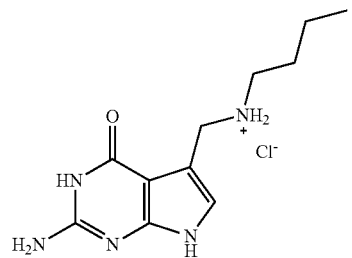 [SMILES: CCCC[NH2+]Cc1c[nH]c2nc(N)[nH]c(=O)c12 ; [Cl-]]

Prepared as per general procedure B using 5-((butylamino)methyl)-2-(tritylamino)-3H-pyrrolo[2,3-d]pyrimidin-4(7H)-one (108 mg, 0.39 mmol) and 1.25 M methanolic HCl (3 cm$^3$) to yield the desired product as a white powder (72 mg, 67%), m.p.>300° C. (decomposition).

$\delta_H$ (400 MHz, DMSO-$d_6$):
0.82 (3H, t, J 7.4), 1.31 (2H, app. sextet), 1.57 (2H, app. quintet), 2.90 (2H, m), 4.12 (2H, t, J 5.3), 6.49 (2H, bs), 6.81 (1H, s), 9.01 (2H, bs), 10.98 (2H, bs), 11.29 (1H, bs)

$\delta_C$ (400 MHz, DMSO-$d_6$):
18.7, 24.7, 32.7, 47.4, 50.6, 103.6 (q), 114.0, 123.2 (q), 153.3 (q), 164.7 (C=O)

HEMS(m/z ESI$^+$):
Found: 236.1518 (M$^+$C$_{11}$H$_{18}$N$_5$O Requires: 236.1511)

$v_{max}$ (film)/cm$^{-1}$:
1456, 1625, 1668, 2443, 2713, 2756, 2873, 2933, 3184

Preparation 9 5-((3-hexylamino)methyl)-2-(tritylamino)-3H-pyrrolo[2,3-d]pyrimidin-4(7H)-one

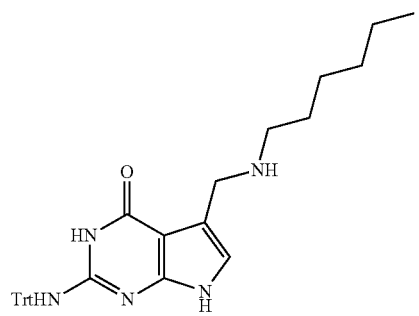

Prepared as per general procedure A using N-((4-oxo-2-(tritylamino)-4,7-dihydro-3H-pyrrolo[2,3-d]pyrimidin-5-yl)methyl)formamide (200.0 mg, 0.48 mmol), n-hexylamine (125.00 µL, 0.95 mmol) and sodium borohydride (55 mg, 1.43 mmol) to yield the desired product as a white powder (200 mg, 83.0%), m.p.>300° C. (decomposition).

$\delta_H$ (400 MHz, DMSO-$d_6$):
0.82 (3H, t, J 7.4), 1.20 (6H, m), 1.34 (2H, app. quintet), 2.40 (2H, t, J 7.4), 3.60 (2H, s), 6.30 (1H, s), 7.23 (15H, m), 7.37 (1H, bs), 10.62 (1H, bs)

$\delta_C$ (400 MHz, DMSO-$d_6$):
14.4, 22.5, 2G.8, 31.G, 29.G, 45.2, 48.3, 70.4 (q), 99.7 (q), 115.2, 116.7 (q), 127.0, 128.1, 129.0, 145.4 (q), 150.1 (q), 150.5 (q), 159.7 (C=O)

$v_{max}$ (film)/cm$^{-1}$:
1552, 1648, 1734, 2856, 2928

HRMS (m/z ESI$^+$):
Found: 504.2769 ([M–H]C$_{32}$H$_{34}$N$_5$O; Requires: 504.2763)

Example 4 N-((2-amino-4-oxo-4,7-dihydro-3H-pyrrolo[2,3-d]pyrimidin-5-yl)methyl)hexan-1-aminium chloride

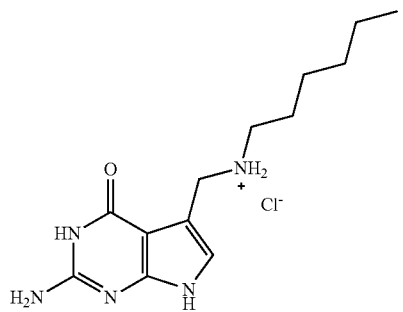 [SMILES: CCCCCC[NH2+]Cc1c[nH]c2nc(N)[nH]c(=O)c12 ; [Cl-]]

Prepared as per general procedure B using 5-((hexylamino)methyl)-2-(tritylamino)-3H-pyrrolo[2,3-d]pyrimidin-4(7H)-one (190 mg, 0.39 mmol) and 1.25 M methanolic HCl (3 cm$^3$) to yield the desired product as a white powder (70 mg, 64.8%), m.p.>300° C.

$\delta_H$ (400 MHz, DMSO-$d_6$):
0.83 (3H, t, J 7.2), 1.25 (6H, m), 1.59 (2H, app. sextet, J 7.2), 2.87 (2H, m), 4.11 (2H, t, J 5.3), 6.71 (2H, bs), 6.84 (1H, d, J 3.6), 9.11 (2H, bs), 11.25 (1H, bs), 11.46 (1H, bs)

$\delta_C$ (400 MHz, DMSO-$d_6$):
14.3, 22.3, 25.8, 25.9, 31.1, 42.6, 46.1, 98.9 (q), 109.3 (q), 118.5, 148.1 (q), 152.8 (q), 159.8 (C=O)

$v_{max}$ (film)/cm$^{-1}$: 1578, 1625, 1669, 2429, 2712, 2861, 2930, 2957, 3266

HRMS (m/z ESI$^+$):
Found: 264.1830 ([M+H ]$^+$C$_{13}$H$_{22}$N$_5$O Requires: 264.1824)

All the examples described herein are TGT substrates.

All the examples described herein are not inhibitors or substrates for HPRT

To assess the potential of these compounds in vivo, a chronic monophasic EAE disease in mice was induced before treatment with the new chemical entity (NCE). EAE Disease was induced in 8-10 week old female mice (C57BL/6) by sub-cutaneous (s.c.) injection of 200 II emulsion containing 150 µg MOG$_{33-55}$ peptide (Genscript) in Complete Freund's Adjuvant (CFA; containing 5 mg/ml heat-inactivated *Mycobacterium tuberculosis*). On the same day, mice were administered 500 ng Pertussis Toxin (Kaketsuken, Japan) intraperitoneally (i.p.) and again two days later. Disease severity was recorded every 24 hours: 0-Normal; 1-flaccid tail; 2-imparied/wobbly gait; 3-complete hind limb weakness; 4-hind limb and forelimb paralysis; 5-moribund state/dead. Protocol is based on the Nature Protocols for Active induction of experimental allergic encephalomyelitis, which includes the scoring methodology:

Stromnes I M, Goverman J M (2006) Active induction of experimental allergic encephalomyelitis. Nat Protoc. 1(4): 1810-9.

Figure 5:
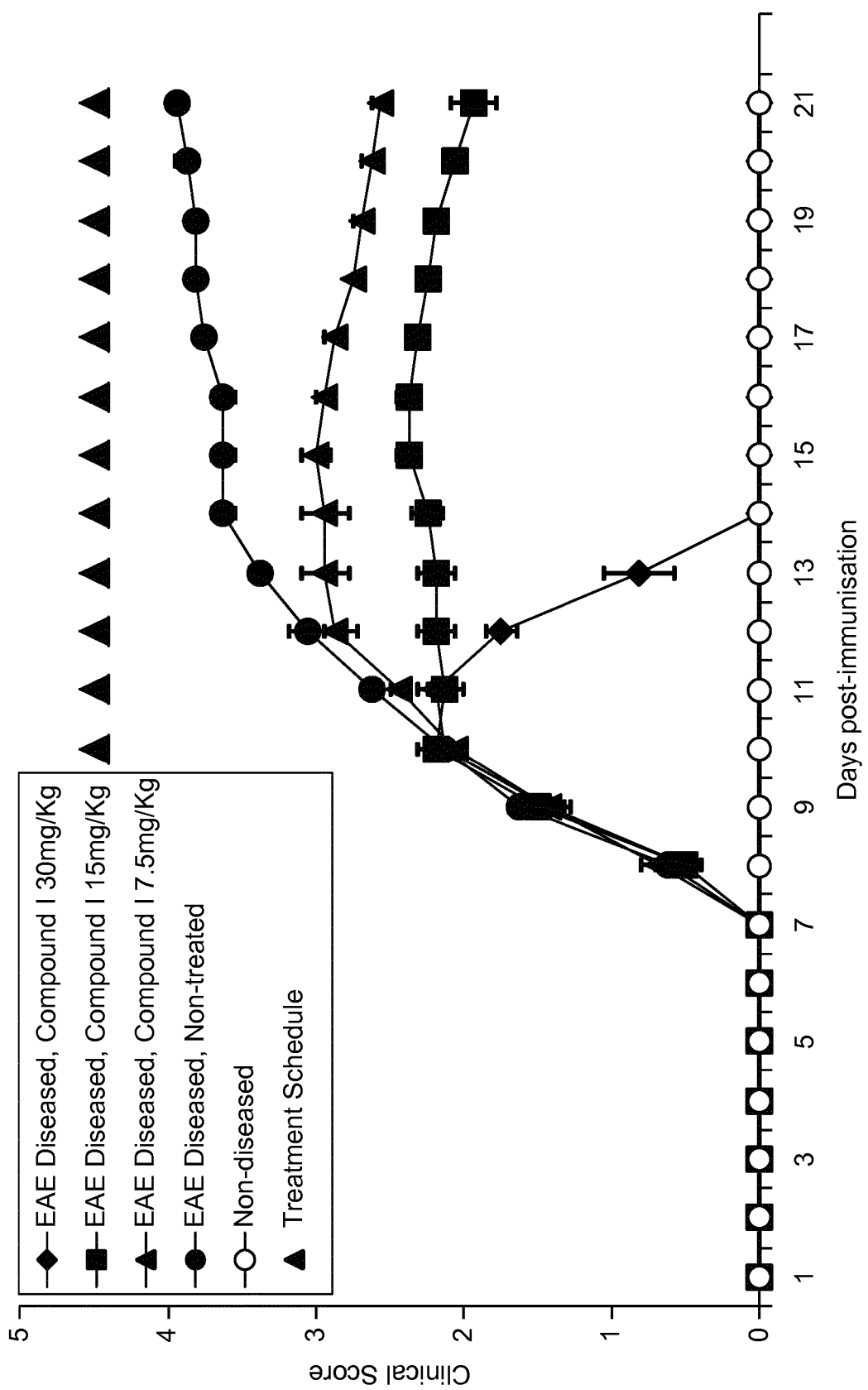
FIG. 5 shows the results of the in vivo testing for molecule N-((2-amino-4-oxo-4,7-dihydro-3H-pyrrolo[2,3-d]pyrimidin-5-yl)methyl)-3-phenylpropan-1-aminium chloride (shown as Compound I)

FIG. 5 shows the results of the in vivo testing for molecule N-((2-amino-4-oxo-4,7-dihydro-3H-pyrrolo[2,3-d]pyrimidin-5-yl)methyl)-3-phenylpropan-1-aminium chloride (shown as Compound I). The EAE score relates to an assessment of disease progression with respect to issues like tail paralysis and limb paralysis, a higher score is a worse condition. A score of 1 indicates decreased tail tone, a score of 2 indicates hind leg weakness (paraparesis), a score of 3 indicates hind limb paralysis and/or incontinence. Note that the untreated animals have a continuous and progressive worsening of disease. In contrast, the animals treated with N-((2-amino-4-oxo-4,7-dihydro-3H-pyrrolo[2,3-d]pyrimidin-5-yl)methyl)-3-phenylpropan-1-aminium chloride (shown as Compound I) exhibit rapid (within 24 hrs) reversal of symptoms at the highest dosage given (30 mg/kg, i.p.) and animals were scored as disease free after 4 daily treatments. At lower doses animals were slower to respond but in all cases disease progression was halted and reversed.

Figure 6:
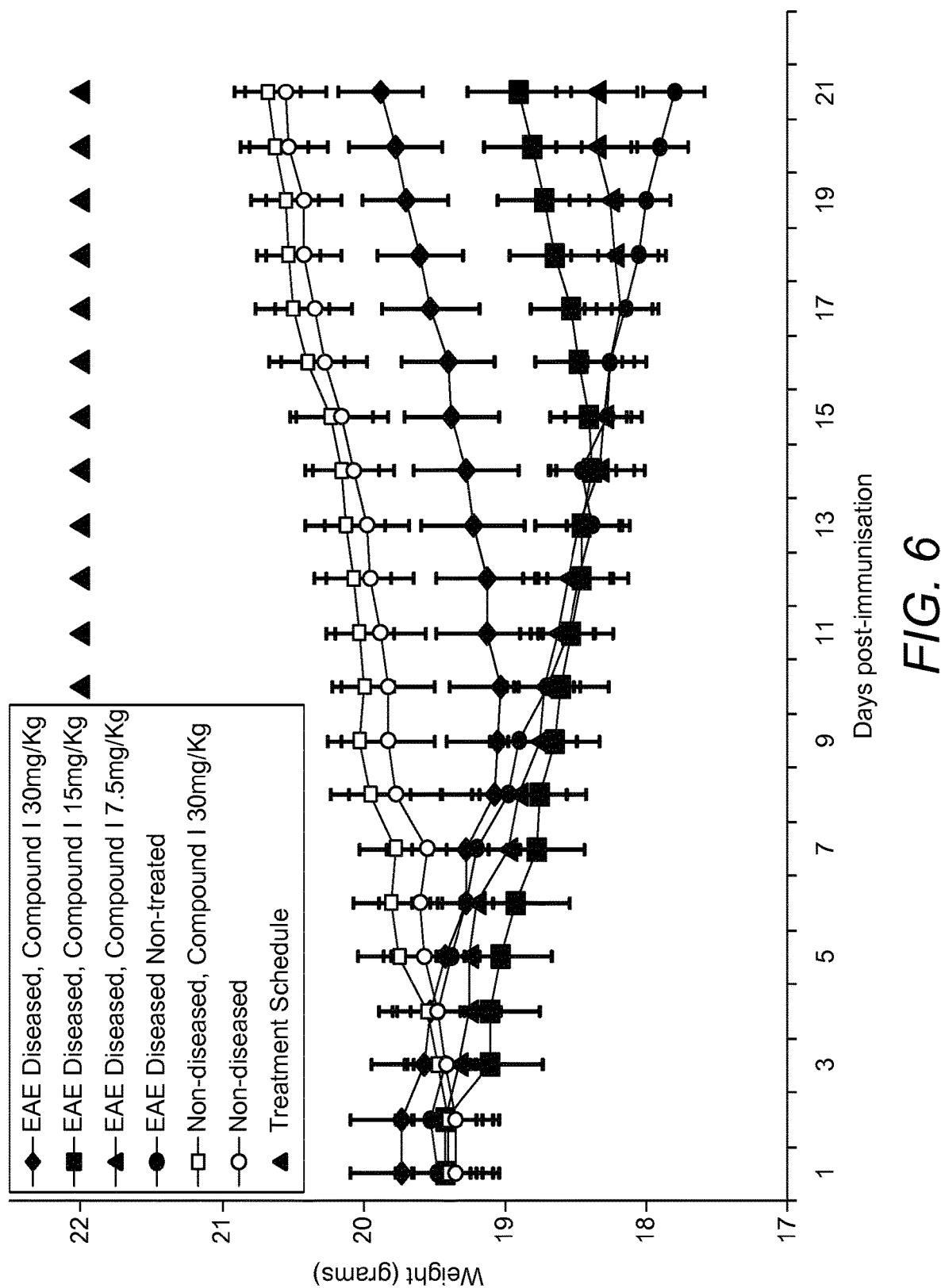
FIG. 6 weight gain/weight loss at various time periods post-immunisation.

FIG. 6 shows that in agreement with the observed disability scores, treated animals showed a dramatic return to normal weight gain, reaching a weight level 96.6% that of controls (19.9 grams versus 20.6 grams), at 21 days post inoculation (dpi). This contrasts with the sustained drop in body weight of non-treated EAE diseased animals to a level 86.4% that of controls at 21 dpi (17.8 grams versus 20.6 grams). Motor coordination and hind-limb strength were also evaluated by the ability of mice to cross a horizontal bar (FIG. 7). Non-diseased animals crossed the bar with an average time of 4.3±0.57 seconds. From 9 dpi, EAE mice showed a rapid deterioration in performance and were subsequently unable to maintain a grip on the apparatus. Strikingly, N-((2-amino-4-oxo-4,7-dihydro-3H-pyrrolo[2,3-d]pyrimidin-5-yl)methyl)-3-phenylpropan-1-aminium chloride (shown as Compound I) treatment fully restored the performance of EAE diseased mice to control levels within 4 treatments.

In addition to the data shown in FIGS. 5, 6 and 7, all the molecules described herein were tested in the chronic EAE model and found to show substantial improvement up to and including reversal of symptoms to a disease free state in subjects.

The invention claimed is:

1. A method of treating a patient diagnosed with a T cell-mediated autoimmune disease comprising administering to the patient an effective amount of a molecule acting as a substrate for a queuine-insertase enzyme complex thereby treating the T cell-mediated autoimmune disease,
wherein the molecule is not a substrate for Hypoxanthine-guanine phosphoribo-syltransferase (HPRT) and treating includes one or more of: reversing the T cell-mediated autoimmune disease, alleviating the T cell-mediated autoimmune disease, or palliatively treating the T cell-mediated autoimmune disease,
wherein the T cell-mediated autoimmune disease is selected from a group consisting of: multiple sclerosis, rheumatoid arthritis, ulcerative colitis, psoriasis, diabetes, inflammatory bowel disease, and Crohn's disease.

2. The method of claim 1, wherein the molecule lowers interferon gamma production.

3. The method of claim 1, wherein the molecule has a displacement of ≥50 pmol in a guanine displacement assay.

4. The method of claim 1, wherein the molecule yields a Guanine Monophosphate (GMP) product in amounts 60% when compared to a control in HPRT assay.

5. The method of claim 1, wherein the molecule lowers interferon gamma production in wild-type cells of the subject in need thereof at a concentration of 100 μM.

6. The method of claim 1, wherein the T cell-mediated autoimmune disease is selected from the group consisting of rheumatoid arthritis, ulcerative colitis, psoriasis, diabetes, and inflammatory bowel disease, and Crohn's disease.

7. The method of claim 6, wherein the T cell-mediated autoimmune disease is Crohn's disease.

8. The method of claim 1, wherein the T cell-mediated autoimmune disease is multiple sclerosis.

9. The method of claim 1, further comprising administering an additional therapeutic agent.

10. The method of claim 9, wherein the additional therapeutic agent is a medicament for the treatment of one or more symptom of multiple sclerosis or symptom associated with multiple sclerosis.

11. A method comprising contacting a mammalian cell with a molecule acting as a substrate for a queuine-insertase enzyme complex to reduce or inhibit endogenous cellular mechanism(s) in the mammalian cell associated with a T cell-mediated autoimmune disease, wherein the molecule is not a substrate for Hypoxanthine-guanine phosphoribosyltransferase (HPRT),
wherein the T cell-mediated autoimmune disease is selected from a group consisting of: multiple sclerosis, rheumatoid arthritis, ulcerative colitis, psoriasis, diabetes, inflammatory bowel disease, and Crohn's disease.

12. The method of claim 11, wherein the molecule lowers interferon gamma production in the mammalian cell.

13. The method of claim 11, wherein the molecule has a displacement of ≥50 pmol in a guanine displacement assay.

14. The method of claim 11, wherein the molecule yields a Guanine Monophosphate (GMP) product in amounts ≥60% when compared to a control in HPRT assay.

15. The method of claim 11, wherein the molecule lowers interferon gamma production in wild-type mammalian cells at a concentration of 100 μM.

16. The method of claim 1, wherein the compound is selected from a group consisting of:
2-amino-5-(((3-phenylpropyl)amino)methyl)-3,7-dihydro-4H-pyrrolo[2,-3-d]pyrimidin-4-one;
N-((2-amino-4-oxo-4,7-dihydro-3H-pyrrolo[2,3-d]pyrimidin-5-yl)methyl)-3-phenylpropan-1-aminium chloride;
2-amino-5-((butylamino)methyl)-3,7-dihydro-4H-pyrrolo[2,3-d]pyrimin-4-one;
N-((2-amino-4-oxo-4,7-dihydro-3H-pyrrolo[2,3-d]pyrimidin-5-yl)methyl)butan-1-aminium chloride;
2-amino-5-((hexylamino)methyl)-3,7-dihydro-4H-pyrrolo[2,3-d]pyrimidin-4-one; and
N-((2-amino-4-oxo-4,7-dihydro-3H-pyrrolo[2,3-d]pyrimidin-5-yl)methyl)hexan-1-aminium chloride.

17. A method of treating a patient diagnosed with multiple sclerosis, comprising administering to the patient an effective amount of 2-amino-5-(((3-phenylpropyl)amino) methyl)-3,7-dihydro-4H-pyrrolo[2,-3-d]pyrimidin-4-one, wherein treating includes one or more of: reversing the multiple sclerosis, alleviating the multiple sclerosis, or palliatively treating the multiple sclerosis.

18. The method of claim 6, wherein the T cell-mediated autoimmune disease is rheumatoid arthritis.

19. The method of claim 1, wherein the compound is 2-amino-5-((((1S,4S,5R)-4,5-dihydroxycyclopent-2-en-1-yl)amino)methyl)-3,7-dihydro-4H-pyrrolo[2,3-d]pyrimidin-4-one.

20. The method of claim 1, wherein the T cell-mediated autoimmune disease is selected from a group consisting of: multiple sclerosis, rheumatoid arthritis, psoriasis, and inflammatory bowel disease, and Crohn's disease.

* * * * *

UNITED STATES PATENT AND TRADEMARK OFFICE
CERTIFICATE OF CORRECTION

| | | |
|---|---|---|
| PATENT NO. | : 11,229,652 B2 | Page 1 of 1 |
| APPLICATION NO. | : 15/976012 | |
| DATED | : January 25, 2022 | |
| INVENTOR(S) | : Vincent Kelly | |

It is certified that error appears in the above-identified patent and that said Letters Patent is hereby corrected as shown below:

On the Title Page

In item (56), References Cited under Foreign Patent Documents, the second reference reads "EP 0089955 A2..." but it should read "EP 0089055 A2..." The twelfth reference reads "WO 20082247 A1..." but it should read "WO 2009082247 A1..."

In the Specification

In Column 19, Line 12, which reads "1545, 1613, 1672, 2870, 2956..." it should read "...2870, 2956...HRMS (m/z ESI+): Found 478.2600 ([M+H]+C30H32N50; Requires 478.2607)...Example 3..."

In the Claims

Column 22, Line 14, Claim 6 reads "...ulcerative colitis, psoriasis, diabetes and inflammatory bowel disease, and Crohn's disease," but it should read "...ulcerative colitis, psoriasis, diabetes, inflammatory bowel disease, and Crohn's disease."

Column 23, Line 9, Claim 20 reads "...multiple sclerosis, rheumatoid arthritis, psoriasis and inflammatory bowel disease and Crohn's disease," but it should read "...multiple sclerosis, rheumatoid arthritis, psoriasis, inflammatory bowel disease, and Crohn's disease."

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*